United States Patent
Balduf et al.

(10) Patent No.: US 9,732,023 B2
(45) Date of Patent: Aug. 15, 2017

(54) PROCESS FOR PREPARATION OF METHACRYLIC ACID AND METHACRYLIC ACID ESTERS

(71) Applicants: Torsten Balduf, Pfungstadt (DE); Steffen Krill, Muehltal (DE); Rudolf Burghardt, Darmstadt (DE)

(72) Inventors: Torsten Balduf, Pfungstadt (DE); Steffen Krill, Muehltal (DE); Rudolf Burghardt, Darmstadt (DE)

(73) Assignee: EVONIK ROEHM GmbH, Darmstadt (DE)

( * ) Notice: Subject to any disclaimer, the term of this patent is extended or adjusted under 35 U.S.C. 154(b) by 0 days.

(21) Appl. No.: 14/773,602

(22) PCT Filed: Mar. 13, 2014

(86) PCT No.: PCT/EP2014/054920
§ 371 (c)(1),
(2) Date: Sep. 8, 2015

(87) PCT Pub. No.: WO2014/146961
PCT Pub. Date: Sep. 25, 2014

(65) Prior Publication Data
US 2016/0031786 A1   Feb. 4, 2016

(30) Foreign Application Priority Data
Mar. 18, 2013  (EP) ..................... 13159831

(51) Int. Cl.
| | |
|---|---|
| C07C 69/52 | (2006.01) |
| C07C 51/25 | (2006.01) |
| C07C 45/75 | (2006.01) |
| C07C 51/44 | (2006.01) |
| C07C 51/48 | (2006.01) |
| B01J 19/24 | (2006.01) |

(52) U.S. Cl.
CPC .......... C07C 51/252 (2013.01); B01J 19/245 (2013.01); C07C 45/75 (2013.01); C07C 51/44 (2013.01); C07C 51/48 (2013.01); B01J 2219/24 (2013.01); Y02P 20/582 (2015.11)

(58) Field of Classification Search
None
See application file for complete search history.

(56) References Cited

U.S. PATENT DOCUMENTS

| | | | | |
|---|---|---|---|---|
| 2,519,788 | A | * | 8/1950 | Payne ..................... C07C 45/38 568/473 |
| 4,262,142 | A | * | 4/1981 | Sherman, Jr. ........... C07C 45/50 568/454 |
| 4,409,128 | A | | 10/1983 | Krabetz et al. |
| 4,487,962 | A | | 12/1984 | Krabetz et al. |
| 4,496,770 | A | | 1/1985 | Duembgen et al. |
| 4,595,778 | A | | 6/1986 | Duembgen et al. |
| 5,248,819 | A | | 9/1993 | Matsumoto et al. |
| 2006/0199975 | A1 | | 9/2006 | Dieterle et al. |
| 2008/0260605 | A1 | | 10/2008 | Dieterle et al. |
| 2010/0120949 | A1 | | 5/2010 | Balduf |
| 2010/0130648 | A1 | | 5/2010 | Balduf et al. |
| 2010/0144931 | A1 | | 6/2010 | Balduf |
| 2010/0273970 | A1 | | 10/2010 | Koestner et al. |
| 2011/0046297 | A1 | | 2/2011 | Hengstermann et al. |
| 2011/0301316 | A1 | | 12/2011 | Dubois |

FOREIGN PATENT DOCUMENTS

| | | |
|---|---|---|
| GB | 1 504 940 | 3/1978 |
| WO | WO 2009/095111 A1 | 8/2009 |

OTHER PUBLICATIONS

U.S. Appl. No. 14/784,320, filed Oct. 14, 2015, Krill, et al.
International Search Report issued May 20, 2014, in PCT/EP2014/054920 filed Mar. 13, 2014.
Written Opinion of the International Searching Authority issued May 20, 2014, in PCT/EP2014/054920 filed Mar. 13, 2014.
European Search Report issued Aug. 9, 2013, in European Patent Application 13159831.0 filed Mar. 18, 2013.
Written Opinion issued May 10, 2016 in Patent Application No. 11201507796V.

\* cited by examiner

*Primary Examiner* — Sudhakar Katakam
*Assistant Examiner* — Ana Z Muresan
(74) *Attorney, Agent, or Firm* — Oblon, McClelland, Maier & Neustadt, L.L.P.

(57) ABSTRACT

The invention relates to a process for preparation of at least one of methacrylic acid and a methacrylic acid ester, comprising the process stepsgas phase oxidation of at least one $C_4$ compound, quenching of the reaction phase, separation and purification of the obtained methacrylic acid and optionally esterification, wherein the $C_4$ compound is a methacrolein comprising mixture, originating from at least two different methacrolein sources, a first methacrolein source being a feed stream obtained by the heterogeneously catalyzed gas phase oxidation of isobutylene or tert-butyl alcohol or isobutylaldehyde or a mixture of two or more thereof, a second methacrolein source being a feed stream obtained by the reaction of propionaldehyde with a $C_1$ extending agent, preferably formaldehyde, and where said methacrolein can be obtained either completely from the first methacrolein source, or completely from the second methacrolein source or from any mixture of both.

17 Claims, 4 Drawing Sheets

PROCESS FOR PREPARATION OF METHACRYLIC ACID AND METHACRYLIC ACID ESTERS

The invention relates to a process for preparation of methacrylic acid, a process for preparation of a methacrylic acid ester and a process for treatment of an aqueous phase comprising at least one organic compound.

Methacrylic acid (MAA) and methacrylic acid esters, such as methyl methacrylate (MMA) and butyl methacrylate are used in a wide variety of applications. The commercial production of methacrylic acid occurs, among other ways, by heterogeneously catalysed gas phase oxidation of isobutylene, tert-butanol, methacrolein or isobutyl aldehyde. The thus obtained, gaseous reaction phase is transformed into an aqueous methacrylic acid solution by cooling and condensing, optionally separated from low-boiling substances such as, for example, acetaldehyde, acetone, acetic acid, acrolein and methacrolein and then introduced into a solvent extraction column, in order to extract and separate methacrylic acid by means of suitable extraction agents, such as, for example, short-chain hydrocarbons. The separated methacrylic acid is further purified, for example by distillation, to separate high-boiling impurities, such as, for example, benzoic acid, maleic acid and terephthalic acid, in order to obtain a pure methacrylic acid. Such a known process is described for example in EP 0 710 643, U.S. Pat. No. 4,618,709, U.S. Pat. No. 4,956,493, EP 386 117 and U.S. Pat. No. 5,248,819.

Another approach is the usage of $C_2$ starting materials, which are extended by suitable chemical reactions to achieve the desired $C_4$ body of methacrylic acid or its derivatives. Ethylene is a widely used starting material for industrial processes via propionaldehyde to methacrylic derivatives and subject matter of numerous review articles and patents.

However, these processes relying on only one single chemical basis are very inflexible, especially in the case of any problems related to the availability or costs of their raw material basis. If any of the $C_2$ or $C_4$ starting materials of one of these processes should run short due to a market or technical disturbance, the whole process would suffer from this without any or only limited capability to act on it.

Methyl tert.-butyl ether for example is a widely used starting material for the $C_4$ based processes. It is an easily transportable starting material, being independent of the presence of a raw material producing plant like a steam cracker in the neighbourhood or a longer pipeline junction. However, as being widely used as an antiknock additive in the automotive field, its price is subjected to drastic changes corresponding to the respective market demand, especially if anywhere a congestion occurs in production capacity.

Ethylene on the other side, if available from a source in direct proximity of a methacrylic acid or methacrylic derivatives production plant, is an appropriate starting material. However, in the event of an industrial disruption or other unforeseen circumstances, or if an alternative raw material basis should become significantly cheaper, even for a limited period, it cannot be reacted to that event if the methacrylic compounds production plant is based on a $C_2$-basis alone.

Therefore it would be desirable to provide a process for the preparation of methacrylic acid or methacrylic acid esters having not that inflexibility related to the starting materials of the process. In an ideal way, the process should allow to perform said production process either alone with a $C_4$ derived starting material or on the other hand alone with a $C_2$ based starting material, and to be able to switch at each time completely to the other basis or to run the process with a mixed mode of the two or more raw material sources.

In addition, such processes generate large amounts of waste water at various process stages, of which the greatest amount is in the form of the aqueous phase remaining after the extraction of the methacrylic acid from the quench phase. The water comes mainly from added steam or water into the gas phase oxidation step and from the use of water as quenching agent in the cooling and condensing step, as well as from the oxidation reaction itself. This waste water contains considerable amounts of organic compounds and cannot be reused or safely disposed of without further treatment to remove at least partially these organic compounds. Such organic compounds generally include desirable products such as methacrylic acid, due to incomplete extraction into the organic extraction agent, as well as other byproducts of the oxidation step such as acrylic acid, acetic acid and propionic acid, which also have commercial value. The organics content in this waste water is generally too high to be compatible with water treatment processes such as biological treatment, for example activated sludge processes, without requiring significant dilution, considerable time and very large treatment facilities, so that in commercial methacrylic acid production the waste water is often combusted, as described, for example, in U.S. Pat. No. 4,618,709. Combustion of waste water is, however, both environmentally and economically unfavourable, requiring high energy input, leading to emissions which may require further treatment before release into the environment, and also leading to loss of potentially valuable organic compounds present in the waste water, as well as loss of the water itself.

It would thus be also advantageous to be able to recover at least partially the organic compounds present in the waste water. It would also be advantageous to recover at least some of the water itself, either with an organics content which is sufficiently low for it to subjected to a biological treatment and/or be discharged into the environment, or in a purity which is sufficient for the water to be reusable, for example as industrial process water or in the methacrylic acid/methyl methacrylate production process itself. CN 1903738 proposes the use of a membrane separator followed by a rectification tower for purifying waste water from acrylic acid production and recovering acrylic acid, toluene and acetic acid. A disadvantage of membrane filtration is that in general large amounts of water—often the waste water itself is used—are required to wash away the components which do not pass through the filter. This washing water with increased concentration of organic compounds must then itself be either further treated or combusted.

Various process steps, in particular the generally distillative separation of the methacrylic acid from the extraction agent following extraction of methacrylic acid out of the aqueous quench phase, result in formation of a methacrylic acid phase as distillate and a high boiler phase as residue—sometimes referred to as bottom phase, as distillation residue or as waste oil—which still contains significant amounts of methacrylic acid. It would be advantageous to be able to recover at least some of this methacrylic acid from the high boiler phase. Various methods have been suggested for treatment of such high boiler phases.

EP 1 043 302 proposes a treatment of waste oil from acrylic acid or methacrylic acid production with a solvent, to prevent polymerisation of the waste oil and/or generation of precipitates in the waste oil. US 2005/0054874 discloses, in an acrylic acid or methacrylic acid synthesis, classifying high-boiling heavy ingredients discharged from individual steps by their acrylic or methacrylic acid content, and treating them by combining them with high boiling phases from other industrial processes, so that they can be stored without precipitation of solids. There is, however, no teaching in either of these documents of recovering methacrylic acid from the waste oil.

An object of the present invention is generally to overcome as far as possible the disadvantages of the prior art processes. In particular it was an object to develop a process for the production of methacrylic acid or a methacrylic acid ester with a reduced formation of by-products and of a clogging that is caused by these by-products.

A further object is to increase the flexibility of the methacrylic acid and/or methyl methacrylate production process in view of the raw material basis by using methacrolein for the oxidation in the gas phase, which is originating from at least two different chemical sources.

A further object is to increase the independence of the methacrylic acid and/or methyl methacrylate production process from up- and downturns of costs and availability of a single raw material source and to increase the security of supply by enabling the process to switch temporarily between at least two different sources.

A further object is to increase the overall yield of the methacrylic acid and/or methyl methacrylate production process by recovering methacrylic acid from high boiler phases.

A further object is to increase the overall efficiency and/or yield of the methacrylic acid production process by recovering organic compounds from process waste water.

Another object of the present invention is to recover water from the process waste water by reducing as far as possible the contamination of this waste water with organic compounds so that the water can be re-used, subjected to a biological purification process, or discharged to the environment, optionally after a biological or other type of purification process, rather than being incinerated together with the organic compounds.

A further object is to increase the overall efficiency and/or yield of the methacrylic acid production process by recovering organic compounds from process waste water.

These objects were solved by providing a novel process characterized in that a $C_4$ compound, especially Methacrolein, is oxidised in step a1) and that this $C_4$ compound thereby originates from a mixture of at least two different $C_4$ compound comprising feed streams.

In detail a contribution to solving the above objects is made by a process for preparation of at least one of methacrylic acid and a methacrylic acid ester, comprising process steps:

a1) gas phase oxidation of at least one $C_4$ compound to obtain a reaction phase comprising methacrylic acid;

a2) quenching of the reaction phase to obtain a crude aqueous phase comprising methacrylic acid;

a3) separation of at least a part of the methacrylic acid from the crude aqueous phase comprising methacrylic acid to obtain at least one crude methacrylic acid-comprising phase a4) separation and optionally purification of at least a part of the methacrylic acid from the crude methacrylic acid-comprising; phase obtained in process step a3) by means of a thermal separation process, a5) optionally, esterification of at least a part of the methacrylic acid obtained in step a4); characterized in that the $C_4$ compound oxidised in step a1) is a methacrolein comprising mixture, wherein said methacrolein can optionally originate from at least two different methacrolein sources, a first methacrolein source being a feed stream obtained by the heterogeneously catalysed gas phase oxidation of isobutylene or tert-butyl alcohol or isobutylaldehyde or a mixture of two or more thereof, a second methacrolein source being a feed stream obtained by the reaction of propionaldehyde with a $C_1$ extending agent, and where said methacrolein can be obtained either completely from the first methacrolein source, or completely from the second methacrolein source or from any mixture of both.

Another contribution to solving the above objects is also made by a process with the steps a1) to a5) as before, which is characterized in that the $C_4$ compound oxidised in step a1) originates from a mixture of at least two different methacrolein comprising feed streams and this mixture comprises 1 to 99 percent by weight of a first methacrolein comprising feed stream obtained by the heterogeneously catalysed gas phase oxidation of isobutylene or tert-butyl alcohol or isobutylaldehyde or a mixture of two or more thereof, and 99 to 1 percent by weight of a second methacrolein comprising feed stream obtained by the reaction of propionaldehyde with a $C_1$ extending agent.

Another contribution to solving the above objects is also made by a process for preparation of at least one of methacrylic acid and a methacrylic acid ester, wherein the separation of at least a part of the methacrylic acid from the crude aqueous phase comprising methacrylic acid coming from the quenching step is extraction of at least a part of the methacrylic acid from the crude aqueous phase comprising methacrylic acid into an organic solvent to obtain a crude organic phase comprising methacrylic acid and a first aqueous phase, wherein the first aqueous phase comprises components i. at least 65 wt. %, preferably in the range of from 65 wt. % to 99.9 wt. %, more preferably in the range of from 70 wt. % to 99.8 wt. % water, yet more preferably in the range of from 75 wt. % to 99 wt. %, more preferably in the range of from 76 wt. % to 98.5 wt. %, more preferably in the range of from 77 wt. % to 98 wt. %, even more preferably in the range of from 78 wt. % to 97.5 wt. %, even more preferably in the range of from 79 wt. % to 95 wt. %, yet more preferably in the range of from 80 wt. % to 90 wt. % water, based on the total weight of the first aqueous phase, and ii. not more than 35 wt. %, preferably in the range of from 0.1 wt. % to 35 wt. %, preferably in the range of from 0.2 wt. % to 30 wt. %, more preferably in the range of from 1 wt. % to 25 wt. %, yet more preferably in the range of from 1.5 wt. % to 24 wt. %, more preferably in the range of from 2 wt. % to 23 wt. %, even more preferably in the range of from 2.5 wt. % to 22 wt. %, even more preferably in the range of from 5 wt. % to 21 wt. %, yet more preferably in the range of from 10 wt. % to 20 wt. % of at least one organic compound, based on the total weight of the first aqueous phase, wherein the sum of the weight amounts of i. and ii. is 100 wt. %

By using in the oxidizing step a1) a methacrolein comprising mixture, wherein said methacrolein originate from at least two different methacrolein sources, a first methacrolein source being a feed stream obtained by the heterogeneously catalysed gas phase oxidation of isobutylene or tert-butyl alcohol or isobutylaldehyde or a mixture of two or more thereof, a second methacrolein source being a feed stream obtained by the reaction of propionaldehyde with a $C_1$ extending agent, and where said methacrolein can be obtained either completely from the first methacrolein source, or completely from the second methacrolein source or from any mixture of both, a flexible choice of raw material depending on their accessibility and price is possible. This makes the process more stable, raw material shortages can easily be solved by fully or partly switching to another raw material base. This makes the process more economic, just because depending on the price development raw material cost optimized mixture can be fed to the oxidation.

On the other hand changing raw material base can lead also to a change of byproducts, which are fed to the methacrolein oxidation reactor. It is possible, that these byproducts or their follow compounds can be found as trace compounds in the methacrylate or methacrylic acid, which could tend to give a coloured product. Especially for optical quality the so called colour number has to be as low as possible. Therefore it is not obvious to the skilled person that a change of raw material base is easily possible.

A surprisingly found advantage of the novel process according to this invention is the higher space-time-yield of the reaction and the better colour number of the oxidized product compared to a process originated exclusively from one of the two Methacrolein sources.

The $C_4$ compound which is subjected to gas phase oxidation in the first methacrolein comprising feed stream in the mixture to be oxidized in step a1) of the process according to the invention is a $C_4$ compound selected from isobutylene, tert-butyl alcohol, isobutylaldehyde, or a mixture of two or more thereof. In a preferred aspect of the invention, the $C_4$ compound is derived from splitting of methyl tert-butyl ether (MTBE) or ethyl tert-butyl ether (ETBE).

The product gas of this $C_4$ based Methacrolein process contains relevant amounts of terephthalic precursors and terephthalic acid itself of 10 to 3000 ppm as by-products. These terephthalic precursors are oxidized to terephthalic acid in the second step. This acid causes clogging during isolation of the methacrylic acid severely in the quench section, but also in the other work-up sections e.g. the extraction of the methacrylic acid.

The terephthalic acid and its derivatives tend to form pyrophoric residues in the connection tubes between first and second stage oxidation reactors, which are potentially auto-ignitable.

Another content of the $C_4$ based Methacrolein containing gas is isobutylene, which may also be formed, if tert-butyl alcohol is used as feed stock for the first stage oxidation. Isobutylene is a known catalyst poison for the second stage oxidation, where Methacrolein is converted to methacrylic acid. Usually heteropoly acids are used as oxidation catalysts used in the oxidation stage a1), these catalysts react very sensible to even traces of isobutylene in the feed gas and show severe deactivation and loss of conversion to methacrylic acid. The product gas contains between 0.1 and 1.5% by volume of isobutylene. In the case that the methacrylic acid synthesis is based on this $C_4$ based Methacrolein source exclusively the conversion of the isobutylene in the first stage must be optimized and maximized. A side effect of this optimization is a reduced yield of Methacrolein and of methacrylic acid as end product. At too high conversions total oxidation of isobutylene becomes predominant, resulting in less Methacrolein yield in the first stage. On the other hand at too low isobutylene conversion the second stage catalyst is poisoned resulting in a lower methacylic acid yield.

The $C_4$ compound which is subjected to gas phase oxidation in the second methacrolein comprising feed stream in the mixture to be oxidized in step a1) of the process according to the invention is preferably obtained by the reaction of propionaldehyde with a $C_1$ extending agent. Such C1-extending agents may be every chemical reagent known to the person skilled in the art, being able to extend a carbon chain by one carbon atom. Most preferred, the $C_4$ compound of the second methacrolein comprising stream is methacrolein.

All reaction suitable to achieve extension by one carbon atom are appropriate, for example all reactions of CH acidic compounds like the Aldol condensation. In a preferred embodiment the $C_4$ compound which is subjected to gas phase oxidation in the second methacrolein comprising feed stream in the mixture to be oxidized in step a1) of the process according to the invention is obtained by the reaction of propionaldehyde with formaldehyde, preferably in the presence of a secondary amine and/or an acid.

This second stream of $C_2$ based Methacrolein contains relevant amounts of Methacrolein dimer, which will be converted in the second stage oxidation to the corresponding acid of the Methacrolein dimer as by-products. These dimers are formed by a Diels-Alder reaction. If Methacrolein is isolated from this process it usually contains 1000 to 20 000 ppm dimer. If this Methacrolein is mixed with air and water for adjusting a appropriate feed gas composition and recycle gas is added to this stream usually the dimer concentration in these combined streams is an amount between 30 ppm and 1000 ppm of this Methacrolein dimer. These by-products have an effect on the oxidation reaction catalyst in the second oxidation stage a1) and can cause a reduced life time of this catalyst.

The $C_4$ compound in the second methacrolein comprising feed stream in the mixture to be oxidized in step a1) of the process according to the invention is preferably obtained from Ethylene (IUPAC name ethene, $C_2H_4$). This $C_2$ building block is widely used in chemical industry and therefore commercially and technically available in large amounts.

Ethylene is produced in the petrochemical industry for example by steam cracking. In this process, gaseous or light liquid hydrocarbons are heated to 750 to 950° C., inducing numerous free radical reactions followed by immediate quenching. This process converts longer hydrocarbon chains into smaller ones and introduces unsaturation. Ethylene is separated from the resulting complex mixture. In another process used in oil refineries, high molecular weight hydrocarbons are cracked over zeolite catalysts. Heavier feedstocks, such as naphtha and gas oils can also be used as stating materials.

Ethylene is converted to propionaldehyde through hydroformylation, in large industrial processes usually by combining synthesis gas with ethylene using a metal, typically rhodium or cobalt catalyst. Synthesis gas (or Syngas) is a fuel gas mixture consisting primarily of hydrogen and carbon monoxide. This hydroformylation is a well known industrial reaction and subject of many reviews, e.g.: Falbe, Jürgen: New Syntheses with Carbon Monoxide. Springer Verlag 1980, Berlin, Heidelberg, N.Y. and Pruett, Roy L.: Hydroformylation. Advances in Organometallic Chemistry Vol. 17, Pages 1-60, 1979 or Robert Franke et al. in the review article "Applied Hydroformylation", Chem Reviews Vol. 112, pages 5657-5732, 2012.

Formaldehyde is available in several forms, e.g. gaseous, in liquid form, preferably as aqueous solution and in solid form, as paraformaldehyde. In a preferred embodiment formaldehyde is formed directly in the production line by the oxidation of methanol, e.g. with air or oxygen in the presence of a catalyst. Suitable catalysts are silver or metal oxides, preferred molybdenum oxide or silver oxide catalysts.

After Ethylene has been hydroformylated to propionaldehyde (propanal) it can be condensed with formaldehyde in a Mannich type reaction to give methacrolein. The Mannich condensation can be carried out in aqueous solution of dimethylamine in the presence of acetic acid to from the Mannich base salt. Methacrolein can be distilled from the resulting solution in a yield of 95%; the aqueous solution can be recycled (EP 58927A1. EP 92097A1).

Alternatively, the crossed aldol condensation of propionaldehyde and formaldehyde (as trioxane) can be conducted over molecular sieves at 300° C. The conversion is around 58% with 98% selectivity to methacrolein. No amine is required (U.S. Pat. No. 4,433,174).

A typical process for the preparation of .alpha.-alkylacroleins like methacrolein by reacting an alkanal with formaldehyde in the presence of a secondary amine and, if desired, of an acid, ca be conducted in the liquid phase under superatmospheric pressure and at above 150° C. (DE 3213681A1).

Methacrolein can be prepared from propionaldehyde and formaldehyde by the process described in German Patent No. 875,194.

A similar process which comprises two stages is described in U.S. Pat. No. 2,848,499. In this process, continuous condensation of propionaldehyde, formaldehyde and secondary amine salts is carried out at 105 to 120° C.

The propionaldehyde is reacted with formaldehyde in stoichiometric amounts, or using an excess of one or other of the reactants; as a rule from 0.9 to 1.5, preferably from 0.95 to 1.2, advantageously from 1 to 1.1, in particular 1 mole of propionaldehyde is employed per mole of formaldehyde. The formaldehyde is advantageously used in aqueous solution which is advantageously from 20 to 60% strength by weight.

The reaction of propionaldehyde with formaldehyde to methacrolein can be carried out in the absence of acids, but is advantageously carried out in the presence of an acid, as a rule an inorganic acid, or of an organic mono-, di- or polycarboxylic acid, preferably a monocarboxylic acid, in particular an aliphatic monocarboxylic acid.

The carboxylic acids that can be used are advantageously the aliphatic monocarboxylic acids having 1 to 10, preferably 2 to 4, carbon atoms, also dicarboxylic acids of 2 to 10, preferably 2 to 6, carbon atoms or polycarboxylic acids of 2 to 10, preferably 4 to 6, carbon atoms. The dicarboxylic acids and polycarboxylic acids can be aromatic, araliphatic or, preferably, aliphatic ones. Examples of suitable acids are acetic acid, propionic acid, methoxyacetic acid, n-butyric acid, isobutyric acid, oxalic acid, succinic acid, tartaric acid, glutaric acid, adipic acid, maleic acid and fumaric acid. Other organic acids can in principle also be used, if the price and availability are acceptable.

The inorganic acids that can be employed are, as a rule, sulfuric acid and phosphoric acid, and also mixtures of acids may be used. From 0 to 0.25, advantageously from 0.01 to 0.1, preferably from 0.02 to 0.05, equivalent of acid is used per mole of propionaldehyde.

Advantageous amines are those of the formula $R_3$—NH—$R_2$ where $R_2$ and $R_3$ are identical or different and are each alkyl of 1 to 10, advantageously 1 to 8, in particular 1 to 4, carbon atoms, which can be further substituted by ether, hydroxyl, secondary amino or tertiary amino groups, in particular by 1 or 2 of these groups, or are each aralkyl of 7 to 12 carbon atoms or cycloalkyl of 5 to 7 carbon atoms, or $R_2$ and $R_3$, together with the adjacent nitrogen, may furthermore be members of a heterocyclic ring which is advantageously 5-membered to 7-membered, can contain a further nitrogen atom and/or an oxygen atom, and can be substituted by hydroxyalkyl or alkyl, each of 1 to 4 carbon atoms.

Examples of suitable amines for the Mannich reaction are dimethylamine, diethylamine, methylethylamine, methylpropylamine, dipropylamine, dibutylamine, diisopropylamine, diisobutylamine, methylisopropylamine, methylisobutylamine, methyl-sec.-butylamine, methyl-(2-methylpentyl)-amine, methyl-(2-ethylhexyl)-amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine and dicyclohexylamine, as well as mixtures of these amines.

The molar equivalent of amine which is used per mole of propionaldehyde is from 0.001 to 0.25, advantageously from 0.01 to 0.1 and preferably from 0.02 to 0.05.

The ratio of the number of equivalents of amine to that of the acid is preferably chosen such that the resulting pH is from 2.5 to 7. The reaction is always carried out at above 150° C., advantageously from 150 to 300° C., preferably from 160 to 220° C., and more preferred from 160 to 210° C. The reaction is performed always under superatmospheric pressure, that is above 1 bar, as a rule from 1 to 300 bar, expediently from 5 to 300 bar, advantageously from 10 to 150 bar, preferably from 20 to 100 bar, and more preferred from 40 to 80 bar. The pressure and temperature are set so that the reaction always takes place at below the boiling point of the reaction mixture. The reaction can be either performed batchwise or, advantageously, in a continuous way.

The residence time or reaction time is not more than 25, expediently from 0.01 to 25, advantageously from 0.015 to 10 minutes, preferably from 0.03 to 1 minutes, more preferred from 0.05 to 0.5 minutes, and most preferred from 0.05 to 0.3 minutes. Where the residence time is less than 10 minutes, a tube reactor is advantageously employed.

The reaction mixture can contain water as well as organic solvents, e.g. propanol, dioxane, tetrahydrofuran or methoxyethanol.

The reaction can be carried out, that a mixture of propionaldehyde, amine, formaldehyde and advantageously water and/or an acid is kept at the reaction temperature and the reaction pressure for the reaction time.

In a preferred embodiment a mixture, advantageously one containing equimolar amounts, of formaldehyde and propionaldehyde (propanal) is heated to the desired reaction temperature by means of a heat exchanger and then fed to a tube reactor. A catalyst solution, i.e. a solution of the secondary amine and an acid, advantageously in water is, if appropriate, likewise heated to the reaction temperature by means of a heat exchanger, and is sprayed into the above mixture at the entrance to the reactor. The highly exothermic reaction takes place, and the reaction mixture becomes hotter. The pressure under which the reaction takes place is kept, by means of a pressure-regulating valve at the reactor exit, at a value such that the reaction mixture still remains liquid during the reaction time, even when the temperature in the reactor is high and/or increases. After the reaction, the mixture is expanded to atmospheric pressure, and is worked up. In the preparation of methacrolein from propanel and formaldehyde, the reaction mixture is preferably fed to a column, where it is stripped with steam. The methacrolein, together with the water, leaves the column at the top, the mixture is condensed, and separated into an upper and a lower phase in a phase-separating vessel, the upper phase, which contains the methacrolein, is collected in a vessel, and the lower phase, which principally comprises water, is recycled to the column to remove any dissolved methacrolein still present in this phase. The aqueous catalyst solution is taken off at the bottom of the column, together with the water formed during the reaction and that initially present in the formaldehyde solution. Where a very small amount of amine has been employed and hence recycling the catalyst is of no value, the bottom liquid can be discarded. However, where the amine concentration in the bottom product is relatively high, water may also be partially distilled off and the catalyst solution recycled to the reactor. Furthermore, the bottom product can be divided into two bleed streams in such a manner that one of these carries exactly that amount of water which corresponds to the amount of water formed during the reaction together with that fed in with the starting materials. This bleed stream is then separated off, and the remaining stream is recycled to the reactor. Aqueous formaldehyde and propanel can also be separately preheated and fed to the reactor.

Separating the reaction mixture by distillation of steam distillation in a column is only one of the possible methods of working up, a further possible procedure being, for example, extraction of the methacrolein from the catalyst solution with a suitable solvent, e.g. 2-ethylhexanol.

The $C_4$ compound oxidised in step a1) is a methacrolein comprising mixture, wherein said methacrolein can optionally originate from at least two different methacrolein sources, a first methacrolein source being a feed stream obtained by the heterogeneously catalysed gas phase oxidation of isobutylene or tert-butyl alcohol or isobutylaldehyde or a mixture of two or more thereof, a second methacrolein source being a feed stream obtained by the reaction of propionaldehyde with a $C_1$ extending agent, preferably formaldehyde, and said methacrolein can be obtained either completely from the first methacrolein source, or completely from the second methacrolein source or from any mixture of both.

These methacrolein comprising mixtures can consist of 1 to 99, 2 to 98, 3 to 97, 5 to 95, 10 to 90, 15 to 85, 20 to 80, 25 to 75, 30 to 70, 35 to 65, 40 to 60, 45 to 55, 48 to 52, 49 to 51, or 50, each value in percent by weight, of a first methacrolein comprising feed stream obtained by the heterogeneously catalysed gas phase oxidation of isobutylene or tert-butyl alcohol or isobutylaldehyde or a mixture of two or more thereof, and
99 to 1, 98 to 2, 97 to 3, 95 to 5, 90 to 10, 85 to 15, 80 to 20, 75 to 25, 70 to 30, 65 to 35, 60 to 40, 55 to 45, 52 to 48, 51 to 49, or 50, each value in percent by weight, of a second methacrolein comprising feed stream obtained by the reaction of propionaldehyde with a $C_1$ extending agent, preferably formaldehyde.

It is clear for the person skilled in the art that if material streams are compared, weight (mass) relations being related to the same time unit are compared (e.g comparison of the flow rate of the streams in kg/h or tons/hour or the like).

The gas phase oxidation in step a1) of the process according to the invention preferably occurs in the presence of at least one oxidation catalyst. If the $C_4$ compound is isobutylene or tert-butyl alcohol, the gas phase oxidation to obtain a methacrylic acid-comprising gas phase can occur in one step, whereby one step in this context is considered to mean that initial oxidation to methacrolein and further oxidation to methacrylic acid occur substantially in the same reaction area, in the presence of at least one catalyst. Alternatively, the gas phase oxidation in step a1) can occur in more than one step, preferably in two steps, preferably in two or more reaction areas separated from each other, whereby two or more catalysts are preferably present, each catalyst preferably being present in a separate reaction area from each other catalyst. In a two-step gas phase oxidation, the first step is preferably at least partial oxidation of the $C_4$ compound to methacrolein, followed by at least partial oxidation of methacrolein to methacrylic acid. Accordingly, for example, in a first reaction step, preferably at least one catalyst suitable for oxidation of at least one $C_4$ compound to methacrolein is present, and in a second reaction step, at least one catalyst suitable for oxidation of methacrolein to methacrylic acid is present.

Suitable reaction conditions for gas phase catalytic oxidation are, for example, temperatures of from about 250° C. to about 450° C., preferably from about 250° C. to about 390° C. and pressures of from about 1 atm. to about 5 atm. The space velocity can vary from about 100 to about 6000 per hr (NTP) and preferably from about 500 to about 3000 per hr. Oxidation, for example gas phase catalytic oxidation, of $C_4$ feeds such as isobutylene to methacrolein and/or methacrylic acid, as well as catalysts therefor, are well known in the literature, for example from U.S. Pat. No. 5,248,819, U.S. Pat. No. 5,231,226, U.S. Pat. No. 5,276,178, U.S. Pat. No. 6,596,901, U.S. Pat. No. 4,652,673, U.S. Pat. No. 6,498,270, U.S. Pat. No. 5,198,579, U.S. Pat. No. 5,583,084.

Particularly preferred catalysts and processes suitable for oxidation of isobutylene or tert-butanol to methacrolein and/or methacrylic acid of the first methacrolein comprising feed stream are described in EP 0 267 556, and particularly preferred catalysts and processes suitable for oxidation of methacrolein or the methacrolein mixture according to the invention to methacrylic acid are described in EP 0 376 117. These documents are hereby introduced as reference and form part of the disclosure of the present invention.

The gas phase oxidation of the methacrolein mixture according to the invention to methacrylic acid preferably occurs at temperatures of from about 250 to about 350° C. and below, at pressures from about 1 to about 3 atm, and at volume loads of from about 800 to about 1800 Nl/l/h.

As oxidising agent, generally oxygen is used, for example, in the form of air, or in the form of pure oxygen or oxygen diluted with at least one gas which is inert under the reaction conditions, such as at least one of nitrogen, carbon monoxide and carbon dioxide, whereby air is preferred as oxidising agent and nitrogen and/or carbon dioxide are preferred as diluent gas. If carbon dioxide is used as diluent gas, this is preferably carbon dioxide recycled from a combustion, preferably a catalytic or thermal combustion of reaction gases and/or byproducts. The gas subjected to gas phase oxidation in step a1) of the process according to the invention preferably also comprises water, which is generally present in the form of water vapour. The oxygen, inert gas or gases and water can be introduced into the reaction phase or combined with the $C_4$ compound before or during or before and during the gas phase reaction.

In a preferred embodiment of the process according to the invention, a mixture comprising at least one $C_4$ compound, air or oxygen and recycled oxidation reactor exit gas, preferably oxidation reactor exit gas which has been combusted prior to recycling, is supplied to step a1). The reactor exit gas preferably comprises at least one unreacted $C_4$ compound, at least one carbon oxide, nitrogen and oxygen, as well as water, depending on the separation conditions and the presence of and action of a combustion step.

In a two-step gas phase oxidation according to the invention, a preferred volume ratio in the first step of $C_4$ compound:$O_2$:$H_2O$:inert gas is generally 1:0.5-5:1-20:3-30, preferably 1:1-3:2-10:7-20. The volume ratio in the second step of the methacrolein mixture:$O_2$:$H_2O$:inert gas is preferably 1:1-5:2-20:3-30, preferably 1:1-4:3-10:7-18.

In step a2) of the process according to the invention, the gas phase which comprises methacrylic acid is cooled and condensed—commonly known as quenching—to obtain a condensate in the form of a crude aqueous methacrylic acid-comprising solution. The condensation can occur by any means known to the skilled person and appearing suitable, for example by cooling the methacrylic acid-comprising gas phase to temperatures below the dew point of at least one of its components, in particular of at least one of water and methacrylic acid. Suitable methods of cooling are known to the skilled person, for example, cooling by means of at least one heat exchanger, or by quenching, for example by spraying the gas phase with a liquid, for example with water, an aqueous composition or an organic solvent, such as, for example, an organic solvent selected from aromatic or aliphatic hydrocarbons, or a mixture of at least two thereof, whereby preferred organic solvents have relatively low vapour pressure under the quenching conditions, such as heptane, toluene or xylene, whereby water is preferred as quench liquid according to the invention, and at least a portion of the condensate formed in the quenching step itself is even more preferred. Suitable quenching processes are known to the skilled person, for example from DE 21 36 396, EP 297 445, EP 297 788, JP 01193240, JP 01242547, JP 01006233, US 2001/0007043, U.S. Pat. No. 6,596,901, U.S. Pat. No. 4,956,493, U.S. Pat. No. 4,618,709, U.S. Pat. No. 5,248,819, whose disclosure concerning quenching of acrylic and methacrylic acids is hereby incorporated and forms part of the present disclosure. It is preferred according to the invention that the gas phase is cooled to temperatures between 40 and 80° C. and washed with water and/or condensate from the quenching step to obtain an aqueous solution comprising methacrylic acid, which can also comprise varying amounts of impurities such as acetic acid, maleic acid, fumaric acid, citraconic acid, acrylic acid and formic acid, as well as aldehydes such as formaldehyde, acetaldehyde, propionaldehyde, acrolein, methacrolein, ketones and unreacted $C_4$ compound or compounds. These impurities, as well as water, need to be separated to the greatest extent possible from the methacrylic acid in order to obtain a high degree of purity of methacrylic acid.

The separation of at least a part of the methacrylic acid from the crude aqueous phase comprising methacrylic acid to obtain at least one crude methacrylic acid-comprising phase can be done in principle by every separating method, but is preferably done by extraction. This extraction in process step a3) occurs by means of an organic extraction agent, for example at least one organic solvent, preferably at least one organic solvent which is substantially immiscible with water, such that an aqueous phase and an organic phase can be formed. Process step a3) also comprises the separation of the aqueous and organic phases from each other. Preferred organic solvents which can be used in step c) of the process according to the invention have a boiling point different to, preferably lower than, the boiling point of methacrylic acid. Preferably, in the process according to the invention, the organic extraction agent used in process step a3) has a boiling point of less than 161° C. measured at atmospheric pressure. The organic extraction agent can then in principle be separated from methacrylic acid, for example by distillation, preferably at least partially, preferably to a substantial extent in step a4) of the process according to the invention, where it is preferably at least partially removed as a low boiler at a higher level in the distillation apparatus than the pure methacrylic acid. The separated organic extraction agent or a part thereof can be conducted back to process step a3), optionally after at least one cooling and/or purification step. Preferred organic solvents for this step are in particular selected from alkanes and aromatic, preferably alkylaromatic, hydrocarbons, whereby at least one organic solvent selected from a $C_6$-$C_8$ hydrocarbon is preferred, whereby heptane, toluene and xylene are particularly preferred and heptane, preferably n-heptane is most preferred. Process step a3) can be carried out by any means known and appearing suitable to the skilled person, preferably as a countercurrent extraction, for example by means of a solvent extraction column, a pulsed fill or packing column, rotating extractors, a washing column, a phase separator or other device suitable for extraction of an aqueous phase with an organic solvent and separation of the organic phase from the aqueous phase. It is preferred according to the invention that at least a part, preferably at least 50 wt. %, preferably at least about 70 wt. %, preferably at least about 80 wt. %, more preferably at least about 90 wt. % of the methacrylic acid comprised in the aqueous methacrylic acid solution is extracted into the organic phase.

Two phases are thus obtained in step a3) of the process according to the invention: a crude organic phase comprising methacrylic acid, which is conducted to step a4) of the process according to the invention, and the first aqueous phase comprising components i. and ii.—water and at least one organic compound—in the amounts described above. Organic compounds which may be comprised as component ii. in the first aqueous phase are any organic compounds which are formed during the gas phase oxidation reaction, such as those mentioned above in connection with the crude aqueous phase obtained in the quenching step, as well as unreacted $C_4$ compounds and any methacrylic acid which has remained in the aqueous phase. While it is possible that the first aqueous phase comprises a small amount of the organic solvent which was used for the extraction in process step a2), for example due to incomplete separation of the organic phase from the first aqueous phase, this solvent is not considered as a component ii.

In step a4) of the process according to the invention, the crude organic phase comprising methacrylic acid obtained in step a3) is subjected to a separation, preferably a thermal separation process to separate at least a part of the methacrylic acid comprised therein from the organic solvent which was used as extraction agent in process step a3). If a thermal separation is used, this is preferably a distillation, whereby organic solvent used for the extraction in process step a3) preferably is removed as head product or at an upper level of a distillation column, preferably at a level in the upper half, preferably at a level in the upper third, of a distillation column, while methacrylic acid or a methacrylic acid-rich phase is removed at a lower level of the distillation column than the extraction solvent. The bottom product in the column, whereby the term "bottom product" also encompasses any phases collected at lower levels of the distillation column than the level or levels at which methacrylic acid phase or phases are collected, is considered as a high boiler phase according to the invention. This bottom product generally comprises components with higher boiling point than methacrylic acid, as well as polymeric materials, together with varying amounts of methacrylic acid, whereby the amount of methacrylic acid can reach up to about 95 wt. % or even more of the total weight of the high boiler phase. It is also possible to use, for example, a fractionating or rectification column, so that impurities with boiling points higher than methacrylic acid remain in the bottom product and methacrylic acid of higher purity can be removed at a level of the column which is higher than that of the bottom product. In this case, the methacrylic acid content of the bottom product (high boiler phase) can be lower than with a simple distillation column. If the organic solvent used for extraction has a higher boiling point than the boiling point of methacrylic acid, it is also possible to remove methacrylic acid phases at the top and/or higher levels of the column compared to the level or levels at which extraction solvent is removed. A further purification of the thus-obtained methacrylic acid or methacrylic acid-rich phase can be by means known to the skilled person, such as by means of a further thermal process, such as distillation or rectification, or by other means such as by crystallisation. Intermediate steps may also be comprised in the process according to the invention, before or during process step a4), such as, for example, any one or more of stripping or distillation to separate low boilers or high boilers, filtration to remove solid impurities, crystallisation, washing and the like. The number of purification and other separation steps depends on the amount of contamination and on the desired purity of the methacrylic acid end product. If the methacrylic acid is to be used as such, for example as a monomer or co-monomer for preparation of a methacrylic acid polymer, a higher purity may be preferred, in particular depending on the end application. If the methacrylic acid is to be esterified, a lower purity of methacrylic acid can be acceptable, for example if the ester end product can be purified more simply, more effectively or more efficiently than the methacrylic acid. As with any thermal process involving methacrylic acid or methacrylic acid ester, the separation and/or purification are preferably carried out in the presence of one or more polymerisation inhibitors.

In a preferred embodiment of the process according to the invention, process step a4) comprises process step aa4) separation of a high boiler phase from the crude organic phase.

In this embodiment of the process according to the invention, the high boiler phase is separated as bottom product in a distillation of the crude organic phase as described above. The term "bottom product" in this context means a product which has been drawn off at the bottom or at a lower level, preferably at a level in about the lower third of a distillation, rectification or fractionation column. The high boiler phase can comprise up to about 95 wt. %, preferably from about 60 wt. % to about 95 wt. %, more preferably from about 65 wt. % to about 90 wt. %, more preferably from about 70 wt. % to about 85 wt. % methacrylic acid, based on the total weight of the high boiler phase, with the remaining weight of the high boiler phase being made up of components with higher boiling points than that of methacrylic acid ("high boilers"), for example high boiling acids such as citraconic acid, maleic acid, terephthalic acid, trimellitic acid and the like, aldehydes such as p-tolualdehyde and benzaldehyde, polymeric materials, in particular polymers of methacrylic acid, as well as polymerisation inhibitors such as, for example, hydroquinone, hydroquinone monomethyl ether, phenothiazine, benzophenothiazine.

It is preferred according to the invention that at least a part, preferably at least 50 wt. %, more preferably at least 60 wt. %, more preferably at least 70 wt. %, yet more preferably at least 80 wt. %, even more preferably at least 90 wt. %, more preferably at least 95 wt. %, yet more preferably all of the high boiler phase separated in process step aa4) is introduced to the first aqueous phase obtained in process step a3) or provided in process step a). In this way, the high boiler phase can be treated together with the first aqueous phase and at least a part of the methacrylic acid comprised in the high boiler phase can be recovered. A small amount of precipitation can occur on combining the first aqueous phase with the high boiler phase, so that an optional solid-liquid separation can be carried out, if necessary, for example if the amount of precipitate is sufficient to negatively influence one or more further process steps, or to interfere with transport of the liquid phase, in particular through pipes, before conducting the liquid phase to further process steps. According to this embodiment of the process according to the invention, references in the present description of the inventive process to the first aqueous phase are also intended to mean the first aqueous phase comprising at least a part of the high boiler phase. This treatment of the high boiler phase with the first aqueous phase—both of which have previously been considered as "waste" phases and generally incinerated—also has the advantage that their treatment is in parallel to the methacrylic acid/methacrylic acid ester production process. This avoids any possible negative influence on the methacrylic acid/methacrylic acid ester production process which might occur by at least partially recycling one or both of these phases directly into the methacrylic acid/methacrylic acid ester production process.

The esterification in process step a5) of at least a part of the thus-obtained methacrylic acid can be carried out in any way known and appearing suitable to the skilled person, optionally in the presence of a polymerisation inhibitor to prevent polymerisation of methacrylic acid and/or methyl methacrylate. The means of carrying out the esterification in step a5) is not particularly limited. The esterification can be carried out, for example, as described in U.S. Pat. No. 6,469,202, JP 1249743, EP 1 254 887, U.S. Pat. No. 4,748,268, U.S. Pat. No. 4,474,981, U.S. Pat. No. 4,956,493 or U.S. Pat. No. 4,464,229 whose disclosures concerning esterification of acrylic and methacrylic acids are hereby incorporated and form part of the present disclosure. A liquid phase esterification is preferred. If the esterification occurs by means of a direct reaction between methacrylic acid and an alcohol it is preferred that the reaction is catalysed by a suitable catalyst. Esterification catalysts are known to the skilled person and include, for example, heterogeneous or homogeneous catalysts such as solid state catalysts or liquid catalysts.

The esterification catalyst is preferably an acidic ion exchange resin such as those described in U.S. Pat. No. 6,469,292, JP 1249743, EP 1 254 887 or commercially available under the trade name names Amberlyst® (Rohm and Haas Corp.), Dowex®, (Dow Corp.) or Lewertit® (Lanxess AG), or an acid capable of catalysing esterification, such as sulphuric acid, $H_2SO_4$.

Methacrylate esters prepared in process step a5) according to the invention preferably have formula $[CH_2=C(CH_3)$ C(=O)O]$_n$—R, and can be formed by esterification of methacrylic acid with an alcohol of formula R(OH)$_m$, whereby n and m represent an integer from 1 to 10, preferably from 1 to 6, more preferably from 1 to 5, more preferably from 1 to 4, more preferably from 1 to 3 and R is selected from the group consisting of linear or branched, saturated or unsaturated, aliphatic or aromatic, ring or straight chain hydrocarbons and linear or branched, saturated or unsaturated, aliphatic or aromatic, ring or straight chain hetero-atom-comprising hydrocarbons, for example alkyls, hydroxyalkyls, aminoalkyls, other nitrogen- and/or oxygen-comprising residues, glycols, diols, triols, bisphenols, fatty acid residues, whereby R preferably represents methyl, ethyl, propyl, iso-propyl, butyl, in particular n-butyl, iso-butyl, hydroxyethyl, preferably 2-hydroxyethyl, and hydroxypropyl, preferably 2-hydroxypropyl or 3-hydroxypropyl, 2-ethylhexyl, isodecyl, cyclohexyl, isobornyl, benzyl, 3,3,5-trimethyl cyclohexyl, stearyl, dimethylaminoethyl, dimethylaminopropyl, 2-tert-butyl aminoethyl, ethyl triglycol, tetrahydrofurfuryl, butyl diglycol, methoxypolyethylene glycol-350, methoxypolyethylene glycol 500, methoxypolyethylene glycol 750, methoxypolyethylene glycol 1000, methoxypolyethylene glycol 2000, methoxypolyethylene glycol 5000, allyl, ethylene glycol, diethylene glycol, triethylene glycol, polyethylene glycol 200, polyethylene glycol 400, 1,3-butanediol, 1,4-butanediol, 1,6-hexanediol, glycerol, diurethane, ethoxylated bisphenol A, ethoxylated bisphenol A with 10 ethylene oxide units; trimethylolpropane, an ethoxylated $C_{16}$-$C_{18}$ fatty alcohol such as, for example, with 25 ethylene oxide units, 2-trimethylammonium ethyl.

The methacrylic acid esters can also be prepared from methyl methacrylate by other methods known to the skilled person, for example by transesterification. In a further possible preparation of the hydroxyester derivatives, methacrylic acid according to the invention can be reacted in a ring-opening reaction with a corresponding oxygen-comprising ring, for example an epoxide, in particular ethylene oxide or propylene oxide.

Preferred methacrylic acid esters are alkyl methacrylates, in particular methyl, ethyl, propyl, iso-propyl, butyl, methacrylates, in particular methyl, n-butyl, iso-butyl, sec-butyl methacrylates, in particular methyl methacrylate, n-butyl methacrylate, isobutyl methacrylate, hydroxyester methacrylate derivatives, for example hydroxyethyl methacrylate, preferably 2-hydroxyethyl methacrylate, and hydroxypropyl methacrylate, preferably 2-hydroxypropyl methacrylate or 3-hydroxypropyl methacrylate, and other methacrylate esters such as ethyl methacrylate, 2-ethylhexyl methacrylate, isodecyl methacrylate, cyclohexyl methacrylate, isobornyl methacrylate, benzyl methacrylate, 3,3,5-trimethyl cyclohexyl methacrylate, stearyl methacrylate, dimethylaminoethyl methacrylate, dimethylaminopropyl methacrylate, 2-tert-butyl aminoethyl methacrylate, ethyl triglycol methacrylate, tetrahydrofurfuryl methacrylate, butyl diglycol methacrylate, methoxypolyethylene glycol-350 methacrylate, methoxypolyethylene glycol 500 methacrylate, methoxypolyethylene glycol 750 methacrylate, methoxypolyethylene glycol 1000 methacrylate, methoxypolyethylene glycol 2000 methacrylate, methoxypolyethylene glycol 5000 methacrylate, allyl methacrylate, a methacrylic ester of an ethoxylated (optionally, for example, with 25 mol EO) $C_{16}$-$C_{18}$ fatty alcohol, 2-trimethylammonium ethyl methacrylate chloride; ethylene glycol dimethacrylate, diethylene glycol dimethacrylate, triethylene glycol dimethacrylate, polyethylene glycol 200 dimethacrylate, polyethylene glycol 400 dimethacrylate, 1,3-butanediol dimethacrylate, 1,4-butanediol dimethacrylate, 1,6-hexanediol dimethacrylate, glycerol dimethacrylate, diurethane dimethacrylate, ethoxylated bisphenol A dimethacrylate, ethoxylated (optionally, for example, with 10 EO) bisphenol A dimethacrylate; trimethylolpropane trimethacrylate, whereby methyl methacrylate, butyl methacrylates and hydroxyester methacrylate derivatives are particularly preferred.

In one aspect of the process according to the invention, the process comprises additionally a separation process step b) which preferably comprises the process steps:

b1a) extraction of at least a part of the first aqueous phase obtained in process step a3) or provided in process step a) with an extraction agent to form the second aqueous phase and an extraction phase comprising at least one component ii.;

b1b) at least partial separation of the second aqueous phase from the extraction phase;

In process step b1a) of the process according to the invention, at least a part, preferably all of the first aqueous phase comprising components i. and ii. is extracted with an extraction agent to form an extraction phase and a second aqueous phase. It is preferred according to the invention that at least a part of at least one component ii. is extracted into the extraction phase, so that the second aqueous phase is depleted in at least one component ii. compared to the first aqueous phase. The extraction preferably takes place at ambient or elevated temperatures, preferably at temperatures in the range of from about 20° C. to about 65° C., more preferably at temperatures in the range of from about 30° C. to about 60° C., yet more preferably at temperatures in the range of from about 40° C. to about 55° C. The extraction is preferably a liquid-liquid extraction. The extraction can be carried out by any means known and appearing suitable to the skilled person, for example by means of an extraction column, a washing column, a phase separator or other device known to the skilled person and appearing suitable for liquid-liquid extraction. Extraction agents which have been found to be suitable for process step b1a) of the process according to the invention are organic solvents, ionic liquids and organic or inorganic oils. Extraction agents—in particular organic solvents—suitable for use in process step b1a) of the process according to the invention are preferably characterised by at least one, preferably at least two, more preferably at least three, more preferably all of the properties i) an average k-value for acetic acid in the system extraction agent—water at 25° C. determined according to the method described herein in the range of from 0.1 to 100, preferably in the range of from 0.2 to 90, more preferably in the range of from 0.3 to 80, yet more preferably in the range of from 0.3 to 70, more preferably in the range of from 0.4 to 60;

ii) an enthalpy of vaporisation of not more than 2260 kJ/kg, preferably of not more than 2000 kJ/kg, preferably of not more than 1500 kJ/kg, more preferably of not more than 1000 kJ/kg, yet more preferably of not more than 800 kJ/kg;

iii) a boiling point in the range of from 35 to 140° C., preferably in the range of from 35 to 125° C., more preferably in the range of from 40 to 120° C., yet more preferably in the range of from 40 to 110° C.;

iv) a solubility in water at a temperature of 25° C., preferably at a temperature of 35° C., more preferably at a temperature of 45° C., yet more preferably at a temperature of 50° C. of not more than 150 g/l, preferably of not more than 130 g/l, more preferably of not more than 110 g/l, yet more preferably of not more than 100 g/l, even more preferably of not more than 90 g/l.

Unless otherwise stated, the above properties are measured at about 50° C. and ambient pressure. The term "k-value" refers to the partition coefficient, i.e. the distribution ratio at equilibrium of the respective organic compound of component ii. of the present invention between the organic (extraction) and the aqueous phases. A k-value of greater than 1 is means that more of the respective organic compound is present in the organic (extraction) phase than in the aqueous phase. While extraction agents with k-values lower than 1 can be used to good effect I the process according to the invention, higher k-values, for example k-values greater than 1 are thus preferred, since they indicate a more complete extraction of organic compounds from the first aqueous phase into the extraction phase. While k-values up to 100 are possible, extraction agents with k-values up to about 5, 10, 20, 30, 40, 50, 60, 70, 80 or 90 can also be preferred according to the invention. Lower k-values, in particular k-values lower than 5 and within the above ranges, can, for example, also be acceptable, in particular if the extraction agent also has one or more of the other preferred properties in advantageous ranges. If the extraction agent is an organic solvent, the enthalpy of vaporisation and the boiling point are preferably as low as possible, within the practical limitations, in particular that the extraction agent is preferably a liquid at the temperature at which the extraction is carried out. The enthalpy of vaporisation is thus preferably not lower than about 22 kJ/mol and the boiling point preferably greater than 0° C. and more preferably not lower than the operating temperature at which extraction is carried out. The enthalpy of vaporisation is preferably not higher than that of water, 2260 kJ/kg or 40.65 kJ/mol, in order to in order to reduce as much as possible the energy input necessary for a thermal separation of any residual extraction agent remaining in the second aqueous phase after separation of the second aqueous phase from the extraction phase in step b1b) of the process according to the invention. The enthalpy of vaporisation is also preferably not higher than that of at least one of the organic compounds of component ii., in order to in order to reduce as much as possible the energy input necessary for a thermal separation of extraction agent from one or more organic compounds of component ii. It is particularly preferred that the enthalpy of vaporisation is not higher than that of at least one of methacrylic acid, acrylic acid and acetic acid. For the same reasons, and to facilitate separation of the extraction agent, the boiling point of the extraction agent is preferably below the boiling point of at least one of the organic compounds of component ii., preferably below the boiling point of at least one of methacrylic acid, acrylic acid and acetic acid, and preferably as low as possible in the preferred ranges. If an ionic liquid or an organic or inorganic oil is used as extraction agent, the enthalpy of vaporisation and the boiling point thereof are preferably as high as possible, preferably higher than at least one of water and at least one organic compound of component ii. The extraction agent preferably has only low solubility in water, in particular at the extraction temperature, and is preferably substantially or completely insoluble in water, as well as being preferably substantially or completely immiscible therewith, in order to enable as complete a separation as possible of the extraction phase and the second aqueous phase.

In step b1b) of the process according to the invention the second aqueous phase is at least partially separated from the extraction phase. The extraction of step b1a) of the process according to the invention and the separation of process step b1b) can be carried out by any means known and appearing suitable to the skilled person, preferably by means of a countercurrent extraction, whereby process steps b1a) and b1b) are preferably carried out in the same device, for example by means of an extraction column, a pulsed fill or packing column, rotating extractors, in particular those using centrifugal force for separation, a washing column, a phase separator or other device suitable for separation of an organic phase or an ionic liquid phase from an aqueous phase. If an organic solvent is used as extraction agent in process step b1a), it is possible to incinerate the extraction phase obtained after the separation in process step b1b). Such an incineration has the advantage that the substantially organic extraction phase acts as a fuel, thus reducing the need to purchase fuel. This option could be preferred, for example, if fuel costs or associated requirements, such as ease and/or cost of transport are disadvantageous and/or the market value of one or more of the organic compounds of component ii. is low, in particular compared to the overall effort and expenditure required for their separation and/or purification.

The second aqueous phase preferably comprises not more than 5.0 wt. %, preferably not more than 4.5 wt. %, more preferably not more than 4.0 wt. %, more preferably not more than 3.5 wt. %, more preferably not more than 3.0 wt. %, even more preferably not more than 2.5 wt. %, based on the total weight of the second aqueous phase, of organic compounds other than the extraction agent used in process step b). The amount of organic compound other than extraction agent in the second aqueous phase is preferably as low as possible and preferably 0 wt. %, although lower limits of 0.5 wt. %, 0.8 wt. %, 1.0 wt. % or 1.2 wt. % can be acceptable. Of the total amount of organic compound in the second aqueous phase, not including any residual extraction agent from process step b1a), in general formaldehyde can represent up to about 1.5 wt. %, based on the total weight of the second aqueous phase, and the remainder is made up of $C_2$ or higher C-chain organic compounds, in particular $C_2$-$C_6$ or $C_2$-$C_4$ compounds. The total amount of such organic compounds depends on the number of extraction steps or extraction cycles comprised in the extraction of process step b1a), and on the amount of extraction agent used in this extraction. A greater number of extraction steps results in a lower organic compound content of the second aqueous phase, but generally also requires a longer and/or multistage extraction, and/or a larger amount of extraction agent, which can lead to a larger volume of extraction phase which must then be further treated or incinerated.

In optional step c) of the process according to the invention, at least one organic compound is at least partially separated from the second aqueous phase, to obtain a third aqueous phase which is depleted in at least one organic compound compared to the second aqueous phase. The third aqueous phase preferably comprises not more than 3 wt. %, preferably not more than 2.8 wt. %, more preferably not more than 2.5 wt. %, more preferably not more than 2.2 wt. %, more preferably not more than 2.0 wt. %, based on the total weight of the third aqueous phase, of organic compounds other than the extraction agent used in process step b1a). The amount of organic compound in the third aqueous phase is preferably as low as possible and preferably 0 wt. %. If organic compound is present in the third aqueous phase, up to about 1.5 wt. % may be in the form of formaldehyde, with the remainder comprising $C_2$ or higher C-chain compounds, in particular $C_2$-$C_6$ or $C_2$-$C_4$ compounds, other than the extraction agent used in process step b1a). The third aqueous phase thus preferably comprises less than 5000 ppm, preferably less than 4000 ppm, more preferably less than 3000 ppm, preferably in the range of from 0 to 3000 ppm, more preferably in the range of from 0 to 2500, more preferably in the range of from 0 to 2200 ppm, most preferably not more than 2000 ppm, based on the total weight of the third aqueous phase, of organic compounds other than $C_1$ compounds (formaldehyde) and other than the extraction agent used in process step b), whereby a lower limit of 500 ppm, or of 1000 ppm, or of 1500 ppm, or of 1800 ppm can be acceptable, depending on the intended further use and/or treatment of the third aqueous phase. The separation in process step c) is preferably a thermal separation, such as a distillation or an azeotropic distillation, preferably at atmospheric pressure. It is preferred that in process step c) residual extraction agent from process step b1a) remaining in the second aqueous phase is separated to the greatest extent possible. If the extraction agent used in process step b1a) forms an azeotrope with water, the separation may comprise an azeotropic distillation, for example an azeotropic distillation using an entrainer. In a preferred aspect of step c) of the process according to the invention, if a separation by distillation, in particular by means of fractional distillation or rectification, is used in process step c), it is preferred that low boiling components, in particular components with lower boiling point than the extraction agent, are separated at the top of the column, extraction agent is drawn off at a side outlet of the column, and any components ii. are drawn off either with the extraction agent or at a further side outlet of the column, preferably at a side outlet which is lower than the side outlet at which extraction agent is drawn off. Any thus separated extraction agent can then be recycled to the extraction in step b1a) of the process according to the invention, corresponding to step h) of the process according to the invention. If one or more organic compounds of component ii. are separated in the same phase as any extraction agent separated in this step, this phase can be added to the extraction phase separated in process step b1b). If one or more organic compounds of component ii. are separated in a different phase to the extraction agent, this different phase can be conducted to step d) or step f) of the process according to the invention. Step c) of the process according to the invention is preferably carried out where an organic solvent has been used as extraction agent in process step b1a) of the inventive process, but it can also be carried out if an ionic liquid or oil extraction was used in process step b1a).

In this aspect of the process according to the invention, the separation in process step d) preferably comprises the process steps d1a) separation of at least a part of the extraction agent from the extraction phase to obtain an extract comprising at least one component ii;

d1b) optionally, separation of at least a part of at least one component ii. from the extract.

In step d1a) of the process according to the invention, the extraction agent used in process step b1a) is at least partially separated from the extraction phase to obtain an extract comprising at least one component ii. If an organic solvent was used as extraction agent, the separation in process step d1a) preferably occurs by means of a thermal separation process. Suitable thermal separation processes are known to the skilled person, whereby distillation, fractionation, rectification and the like are preferred according to the invention, whereby a vacuum distillation is preferred. One or more separation processes can be comprised in process step d1a) according to the invention. In a preferred thermal separation process, where the organic solvent used as extraction agent in process step b1a) has a lower boiling point than one or more components ii. to be separated, the extraction agent is removed at the head of a distillation column, or at an upper level or upper levels of a fractionation column or a rectification column, preferably in the upper half of the column, and one or more components ii. or an extract comprising at least one component ii. are removed at a lower level, at lower levels, relative to the level at which the extraction agent is removed, or at the bottom of the column. An advantage of using an organic solvent with boiling point lower than that of at least one component ii. as extraction agent in process step b1a) is that some or all of the components ii., in particular methacrylic acid and acrylic acid, are thermally sensitive and tend increasingly to dimerise, oligomerise or polymerise as the temperature increases. Thermal treatment of these compounds at elevated temperature thus generally requires the addition of polymerisation inhibitors. If a lower boiling extraction agent is to be separated, and/or if the separation is a vacuum distillation, this separation can be carried out at lower temperatures, below the boiling point of the respective component ii., reducing the tendency to polymerise and thus also reducing the need for polymerisation inhibitor.

If an ionic liquid or an organic or inorganic oil was used as extraction agent in process step b), the separation in process step e) preferably occurs by phase separation or evaporation, preferably by evaporation of the volatile component or components.

The separation in process step d1b) is preferably a thermal separation process, preferably a distillation, fractionation or rectification, preferably a vacuum distillation, whereby at least a part of at least one component ii. is separated from the extract. The extract can comprise, for example, in addition to at least one component ii. to be separated, extraction agent or other components ii. If more than one component ii. is comprised in the extract, for example two or more components ii., it is possible that only one component ii. is separated in process step d1b), or that two or more components ii. are separated. The selection of distillation, fractionation or rectification as separation means can be easily determined by the skilled person and depends principally on the number and amount of other compounds in the extract from which the at least one component ii. is to be separated, as well as on the respective boiling points of the one or more components ii. to be separated and of the components of the extract which are not intended to be separated, in particular the proximity of the boiling points of the other components of the extract to the boiling point of the at least one component ii. to be separated and, if more than one component ii. is to be separated, the proximity of the boiling points of the components ii. to be separated to each other. Another factor to consider is the desired purity of the at least one component ii. to be separated. Further purification of the at least one component ii. can be desirable or even necessary following the separation in step f) of the process according to the invention.

In a further aspect of the process according to the invention, the separation in process step b) preferably comprises the process steps:

b2a) crystallisation of at least a part of the water from at least a part of the first aqueous phase obtained in process step a3) to form a crystallised aqueous phase as second aqueous phase and a mother liquor, wherein the mother liquor comprises at least one component ii.;

b2b) at least partial separation of the crystallised aqueous phase from the mother liquor.

In process step b2a) of the process according to the invention, at least a part of the first aqueous phase is subjected to a crystallisation to obtain a crystallised aqueous phase, in which the water of this phase is present in crystallised form, and a mother liquor comprising at least one component ii. The crystallisation in process step b2a) can occur by methods known to the skilled person for continuous or batchwise, preferably continuous crystallisation, such as dynamic or static crystallisation or a combination of the two, for example melt crystallisation, scratch cooling crystallisation, fractional crystallisation, layer crystallisation, suspension crystallisation, falling film crystallisation and the like, or any combination of two or more thereof, whereby suspension melt crystallisation is preferred, preferably in a continuous crystallisation process. In a preferred aspect of step b) of the process according to the invention, the crystallisation can occur in two stages, whereby in a first stage crystals form, for example on a cooled surface, and in a second stage these crystals are allowed to grow and increase in size. The two stages can take place in substantially the same area as each other, or each stage can take place in a separate area. If a suspension melt crystallisation is carried out in the process according to the invention, it is preferred that the crystallisation occurs in at least one crystallisation and melting cycle. In a preferred aspect of a suspension melt crystallisation according to the invention, at least a part of the melted crystallised water is used to wash at least a part of the crystallised water. Suitable processes are described, for example, with reference to purification of acrylic acid and/or methacrylic acid, in WO 02/055469, WO 99/14181 WO 01/77056, U.S. Pat. No. 5,504,247, whose disclosure concerning crystallisation, in particular suspension melt crystallisation as disclosed in WO 01/77056 and WO 02/055469, is hereby incorporated by reference and forms part of the present disclosure. If water forms a eutectic mixture with one or more components ii. in the first aqueous phase, in order to obtain water in the crystallised (second) aqueous phase which is as pure as possible water is preferably only crystallised out to around the eutectic point.

In step b2b) of the process according to the invention the crystallised aqueous phase as second aqueous phase is at least partially separated from the mother liquor. The separation can be carried out by any means known and appearing suitable to the skilled person, preferably by means of at least one of a filtration, a centrifugation, a phase separation or other solid-liquid separation means, preferably a filtration, a centrifugation, or a phase separation, whereby a washing of the crystals may also be comprised, for example a washing with at least one of mother liquor, melted crystallised aqueous phase, and water. Such a wash-melt-type crystallisation and separation is described, for example in the references cited above with respect to process step b2a). In a preferred aspect of step b2b) of the process according to the invention, a phase separation, preferably in a wash column, for example a wash column of the type disclosed in WO 01/77056, is used whereby the crystallised phase floats on and/or in the mother liquor, and/or is collected and/or compacted, for example by means of a movable plate which moves upwards in the column and allows mother liquor to pass through while retaining the crystallised phase on the plate, for example a plate in the form of a filter, so that the crystallised phase can be removed at the top or at an upper level of the wash column, while the mother liquor passes through the plate and is removed at a lower level of the phase separator compared to the crystallised phase. It is also possible that the crystallised phase is separated at a lower level of a phase separator, for example depending on the relative densities of the crystallised aqueous phase and the mother liquor, or the device used for crystallisation and/or separation. In this aspect, at least a part of the crystallised phase can be melted, for example in a heat exchanger, and conducted back to the wash column as wash liquid to wash the crystallised phase present in the wash column, preferably in countercurrent flow. In another preferred embodiment of step c) of the process according to the invention the separation is carried out by centrifugation. In this embodiment at least a part of the crystallised phase can be melted, for example in a heat exchanger, and conducted back to the centrifugation device as wash liquid to wash crystallised phase present in the centrifugation device. Since the mother liquor is depleted in water and comprises a greater proportion of organic components compared to the first aqueous phase, it is possible to incinerate the mother liquor obtained after the separation in process step b2b). Such an incineration has the advantage that this substantially organic phase, with reduced water content compared to the first aqueous phase, can act as a fuel, thus reducing the need to purchase fuel. This option could be preferred, for example, if fuel costs or associated requirements, such as ease and/or cost of transport are disadvantageous and/or the market value of one or more of the organic compounds of component ii. is low, in particular compared to the overall effort and expenditure required for their separation and/or purification.

In a preferred aspect of the process according to the invention, steps b2a) and b2b) are carried out continuously. The crystallisation step b2a) may take place in a crystallisation unit suitable for carrying out step b2a) of the process according to the invention, which is optionally connected to a separation unit suitable for carrying out step b2b) of the process according to the invention, such as a wash unit or a centrifugation device, as described above. The crystallisation unit may comprise one or two stages, corresponding to the possible two stages of process step b2a). In the crystallisation unit, or in the first stage of a crystallisation unit, the first aqueous phase is generally cooled so that water at least partially crystallises out. If crystals form at least partially on cooled surfaces of the crystallisation unit, these can be scraped off. The resulting slurry is then optionally conducted to the second stage of the crystallisation unit, if a second stage is comprised, where the slurry is preferably stirred while more crystals grow and/or crystal size increases. From the crystallisation unit the crystal/mother liquor slurry is then conducted to the separation unit, where the solid crystals are at least partially separated and optionally washed to at least partially remove impurities. At least a part of the optionally washed crystals can be melted and at least a part of the melted part can be either conducted to, or treated in, a further process step, for example at least one biological purification treatment, use as process water or conducting to at least one of process steps a1) and a2), as described below, or used as wash liquid, whereby it is possible that a first part of the melted crystallised phase is handled as described below and a further part of the melted crystallised phase is used as wash liquid for washing the crystals. It is also possible that at least a part of the crystals is supplied to the crystallisation unit as crystallisation seed. A melting step may also be comprised. The melting step may be effected by means of a device which may be internal or external to at least one of the crystallisation unit and the wash unit. The crystallisation unit can be any crystallisation unit known to the skilled person and appearing suitable for crystallisation of water from an aqueous solution comprising organic components. Suitable crystallisation units, as well as crystallisation units incorporating wash and/or melt units are those commercially available from Sulzer Chemtech AG, Switzerland or Niro Process Technology B.V., The Netherlands. Examples of suitable crystallisation units, wash units and melting units, as well as combined crystallisation/wash/melt units are given in the literature cited above in connection with process step b2a). Centrifugation devices suitable for the process according to the invention are known to the skilled person.

Process steps b2a) and b2b) can, but do not necessarily result in complete crystallisation of water out of the first aqueous phase, so that the mother liquor can, or even generally does, comprise a certain amount of water. This is, for example, particularly the case if water forms a eutectic mixture with one or more of the components ii. of the first aqueous phase. In this case, in order to obtain water in the crystallised (second) aqueous phase which is as pure as possible, water is preferably only crystallised out to around the eutectic point, so that a proportion of water remains in the mother liquor. The proportion of water remaining in the mother liquor thus depends on the type and amount of the respective components ii. in the first aqueous phase with which water forms a eutectic mixture, and the respective eutectic point of water with this or these components ii. In a further aspect of the process according to the invention, the separation in process step d) preferably comprises at least one of the process steps:

d2a) at least partial dewatering of the mother liquor separated in process step b2b) to obtain an at least partially dewatered mother liquor;

d2b) separation of at least a part of at least one component ii. from the mother liquor obtained in process step b2b) or from the at least partially dewatered mother liquor obtained in process step d2a).

In a preferred aspect of the process according to the invention, at least a part of the water remaining in the mother liquor after the crystallisation is separated from the mother liquor in process step d2a). The dewatering in process step d2b) preferably occurs by means of an azeotropic distillation, preferably an azeotropic distillation using an entrainer. Any entrainer known to the skilled person and appearing suitable for the at least partial dewatering of the mother liquor separated in process step b2b) can be considered. Particularly preferred entrainers according to the invention are linear or branched alkanes, especially heptane or hexane, cycloalkanes, especially cyclohexane, acetates, especially isobutyl acetate or ethyl acetate, aromatic compounds, especially toluene or benzene, or $CS_2$, $CCl_4$ or bromo methane.

The separation in process step d2b) is preferably a thermal separation process, preferably a distillation, fractionation or rectification, whereby at least a part of at least one component ii. is separated from the mother liquor or from the dewatered mother liquor. The mother liquor or the dewatered mother liquor can comprise, for example, in addition to at least one component ii. to be separated, extraction agent from step a3) of the process according to the invention, or other components ii. If more than one component ii. is comprised in the mother liquor or the dewatered mother liquor, for example two or more components ii., it is possible that only one component ii. is separated in process step d2b), or that two or more components ii. are separated. The selection of distillation, fractionation or rectification as separation means can be easily made by the skilled person and depends on a number of factors, for example on the number and amount of other compounds in the mother liquor or the dewatered mother liquor from which the at least one component ii. is to be separated, as well as the respective boiling points of the one or more components ii. to be separated and of the components of the mother liquor or the dewatered mother liquor which are not intended to be separated, in particular the proximity of the boiling points of the other components of the mother liquor or the dewatered mother liquor to the boiling point of the at least one component ii. to be separated and, if more than one component ii. is to be separated, the proximity of the boiling points of the components ii. to be separated to each other. Another factor to consider is the desired purity of the at least one component ii. to be separated.

According to this aspect of the process according to the invention, the process preferably further comprises the process step e2) melting of the crystallised aqueous phase to obtain a melted crystallised aqueous phase as third aqueous phase.

The melting of the crystallised aqueous phase can occur by any means known to the skilled person and appearing suitable. In particular, the crystallised aqueous phase can be subjected to a temperature at which is melts, for example in a melting device or a heat exchanger. The melting in process step e2) can correspond to the melting already mentioned in the description of process steps b2a) and b2b), and/or it can be a further melting. Thus, for example, a first melting might be carried out within the scope of process steps b2a) and b2b), for example in order to provide a wash liquid for washing the crystals. The wash liquid itself then preferably at least partially crystallises on the crystals as it contacts them. The thus washed and then separated crystals can be melted again to provide a wash liquid, in as many wash-melt cycles as are necessary to obtain a desired crystal purity. Once a desired purity has been obtained, the crystals can then be melted in step e2) of the process according to the invention, and further conducted to at least one of biological purification treatment, being used as process water, and at least one of process steps a1) and a2).

The melted crystallised aqueous phase, or third aqueous phase, according to this aspect of the invention is generally of sufficient purity to be usable directly as process water or as added water in process steps a1) or a2) of the process according to the invention. In particular, the crystallised aqueous phase or the melted crystallised aqueous phase preferably comprises less than 5000 ppm, preferably less than 4000 ppm, more preferably less than 3000 ppm, preferably in the range of from 1500 to 2500 ppm, more preferably in the range of from 1800 to 2200 ppm, most preferably not more than 2000 ppm, based on the total weight of the respective aqueous phase, of organic compound. It is possible to achieve lower amounts of impurities, for example less than about 500 ppm, or even less than 100 ppm and in the range of from 0 ppm to 100 ppm, in particular by employing a large number of wash-melt cycles in process step c) according to the invention. These lower amounts of impurities are, however, generally only obtained together with a reduced amount of water. A biological purification treatment can optionally be carried out before use as process water or as added water in process steps a1) or a2). If the water of the melted crystallised aqueous phase is to be used for other purposes or discharged into the environment it can be preferred but is not always necessary that such use or discharge follows a biological purification.

It is preferred according to the invention that the third aqueous phase is subjected to at least one of being conducted to at least one biological purification treatment, being used as process water, and being conducted to at least one of process steps a1) and a2).

The term "biological purification treatment" in the context of the present invention is intended to mean any treatment which increases the purity of water, for example by removing contaminants or impurities, preferably organic contaminants, by means of one or more biological organisms and/or microorganisms or biologically or biochemically active substances, for example substances derived from such organisms or microorganisms. The contaminants and impurities to be removed in this way are generally the organic compounds remaining in the third aqueous phase. The removal is effected by digestion or breaking down of some or all of the organic compounds. Increased purity of water is measured, for example, by a decrease in contaminants and/or impurities, and/or by a decrease in the water's biochemical oxygen demand (BOD) or chemical oxygen demand (COD), preferably to levels which mean the waste water can be reused, for example as industrial process water, in the process according to the invention, in particular in one or both of process steps a1) or a2), or discharged into the environment or into a water supply chain, depending on the purity achieved. Biological purification treatments are known to the skilled person and can be, for example, one or more of a so-called activated sludge treatment. Such treatments are conventional and well known to the person skilled in the art. The biological purification treatment can be carried out in one or more stages, and may be continuous or discontinuous.

If the third aqueous phase is subjected to at least one biological purification treatment this treatment is preferably at least one of an aerobic treatment and an anaerobic treatment. In one embodiment of a treatment having two or more stages, for example, a first anaerobic treatment can be followed by an aerobic treatment, a first aerobic treatment can be followed by an anaerobic treatment, or a sequence of aerobic and/or anaerobic treatments can be used, as for example in a sequential batch reactor.

If the separation in process step d) of the process according to the invention is a thermal separation, it may not always be possible, or, for example, economically or technically practical to separate components from each other, for example if two or more components have very similar boiling points. This may be particularly the case if the mother liquor or the dewatered mother liquor which is subjected to process step d) comprises a relatively large number of components, in particular if one or more components ii. have similar boiling points to the at least one component ii. which is to be separated in process step d), making a fine tuning of the separation for just one component ii. in process step d) more difficult. It can then be more appropriate or more practical to separate two or more components ii. in the further process step f), where such an adaptation for the specific separation requirements of the respective components ii. may be more easily achieved. Accordingly, in an aspect of the process according to the invention, the at least one component ii. separated in process step d) can be a mixture of at least two components ii. and in a further process step f) at least one component ii. is preferably at least partially separated from this mixture. The separation in process step f) of the process according to the invention may comprise one or more separation steps, such as a thermal separation, as already discussed above for other separation steps in the process according to the invention, a chromatographic separation, a chemical separation, for example by preferential reaction of one component ii. to form a reaction product which is more easily separable from the one or more other components ii. or by reaction of two or more components ii. to form reaction products which are more easily separable from each other, or any other separation means known and appearing suitable to the skilled person.

In a preferred embodiment of the process according to the invention, the at least one organic compound of component ii., preferably the at least one component ii. which is at least partially separated in process step f), is at least one organic compound selected from carboxylic acids, aldehydes and ketones. Among these, it is preferred according to the invention that the at least one component ii., preferably the at least one component ii. which is at least partially separated in process step f), is at least one of acetic acid, acrylic acid, propionic acid and methacrylic acid.

If the at least one component ii. separated in at least one of process steps d) and f) is or comprises methacrylic acid, in a preferred embodiment of the process according to the invention at least a part of this methacrylic acid phase is added to the crude aqueous phase obtained in process step a2) and/or to the crude organic phase obtained in process step a3). This embodiment can be preferred, for example if the methacrylic acid separated in one or more of process steps d) and f) is not of the purity desired for its end use. Addition to the crude aqueous phase might be preferred, for example, if the separated methacrylic has been separated together with one or more other components with boiling point lower than methacrylic acid. Addition to the crude organic phase can be preferred, for example, if the components other than methacrylic acid have higher boiling points than methacrylic acid, since such higher boilers can be separated in process step a4). While the relative proportions of methacrylic acid to other components, in particular to other components ii., can also play a role, the nature of the other components in the at least one component ii. separated in at least one of process steps e), f) and j) has greater weight in deciding to which phase this methacrylic acid-comprising phase separated in at least one of process steps e), f) and j) is added. For example, if the methacrylic acid separated in at least one of process steps d) and f) is relatively pure, comprising, for example, not more than about 5 wt. %, preferably not more than about 4 wt. %, preferably not more than about 3 wt. %, preferably not more than about 2 wt. %, preferably in the range of from about 1 wt. % to about 2 wt. % of impurities or other components ii., it can be preferred to introduce this methacrylic acid into the optional purification step of process step a4).

In another aspect of the process according to the invention, at least a part of the at least one component ii. separated in at least one of process steps d) and f), or at least a part of the first aqueous phase obtained in process step a3), is subjected to a process step g) esterification to obtain an ester phase comprising at least one ester.

This step can be preferred if the respective at least one component ii. is a carboxylic acid. The details of the esterification step are the same as those described above for process step a5) of the process according to the invention. An esterification of at least one component ii. separated in at least one of process steps d) and f), rather than or in addition to obtaining the respective at least one component ii. itself, can be preferred, depending, for example, on the obtainable purity of the separated respective component ii., on the market or further applications for the respective component ii. compared to its ester. An esterification of at least one component ii. comprised in the first aqueous phase obtained in process step a3) can be preferred, for example, if the first aqueous phase comprises only a small proportion of impurities and/or components ii. which are not intended to be separated, for example a total amount of impurities of less than about 6 wt. %, preferably less than about 5 wt. %, preferably less than about 4 wt. %, more preferably less than about 3 wt. %, based on the total weight of the first aqueous phase, of impurities and/or components ii. which are not intended to be separated, based on the total weight of the first aqueous phase, in particular impurities which can be, for example, more easily separated from an ester of a respective component ii. than from the component ii. itself.

Particularly preferred esters comprised in the ester phase according to the invention are based on a $C_1$-$C_4$ carboxylic acid and a $C_1$-$C_4$ alcohol, whereby esters based on a $C_2$-$C_4$ carboxylic acid are preferred. Particularly preferred esters, in addition to the methacrylate esters mentioned in connection with process steps a5), are methyl acetate, ethyl acetate, n-propyl acetate, isopropyl acetate, n-butyl acetate, isobutyl acetate, sec-butyl acetate, methyl acrylate, ethyl acrylate, n-propyl acrylate, isopropyl acrylate, n-butyl acrylate, isobutyl acrylate, sec-butyl acrylate, methyl propionate, ethyl propionate, n-propyl propionate, isopropyl propionate, n-butyl propionate, isobutyl propionate, sec-butyl propionate, of which the acetates and the acrylates are preferred.

It is possible according to the invention that the ester phase comprises at least two esters. This can be the case if the at least one component ii. separated in at least one of process steps d) and f), or at least a part of the first aqueous phase obtained in process step a3) comprises at least two components ii. which are capable of reacting to form an ester, in particular at least two carboxylic acids. This embodiment can be preferred if the at least two components ii. which are capable of reacting to form an ester are particularly difficult to separate, for example by thermal or other means, for example where their properties such as boiling point, solubility in a given solvent and/or volatility are very close, whereas their esters can be separated from each other with less difficulty.

The process according to the invention can further comprise the process steps h) at least partial separation of at least one ester from the ester phase;

j) optionally, purification of the at least one ester separated in process step h).

In general, in addition to the at least one ester, the ester phase can comprise solvent, for example water or at least one organic solvent suitable for an esterification reaction, or a mixture thereof, as well as unreacted component ii., and possibly also further ester or esters. The separation in process step h) may be by any separation means known to the skilled person and appearing suitable for separating the respective ester from the ester phase. Examples of suitable separation means are, for example, thermal separation, such as distillation, fractionation or rectification, separation means based on different solubility of the at least one ester compared to other components of the ester phase, solid-liquid separation means such as filtration, among others. If necessary or desired, a purification of the at least one ester separated in process step h) can also be carried out. The purification means depends on the ester, whereby, for example, purification by thermal means, by chromatographic means, by washing, or by crystallisation can all be considered.

In a preferred embodiment of the process according to the invention, at least a part of the at least one ester obtained in at least one of process steps g), h) and j) can be used as extraction agent in process step b1a).

In an embodiment of the process according to the invention, the process to provide the $C_4$ compound of the first methacrolein comprising feed stream further comprises the step aa1) splitting of methyl tert-butyl ether (MTBE) to obtain at least one $C_4$ compound and methanol, wherein at least a part of the at least one $C_4$ compound is supplied as feed to the gas phase oxidation of at least one of process steps a1) and alpha1). MTBE is widely used as feedstock for isobutylene and splitting of MTBE is well known in the art. Splitting of MTBE can occur by any suitable means which are known to the skilled person. Suitable catalysts and reaction conditions are described, for example, in EP 1 149 814, WO 04/018393, WO 04/052809; Ullmann's Encyclopedia of Industrial Chemistry, 5$^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, 5$^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein. The disclosures of these references are hereby incorporated by reference and form part of the disclosure of the present invention.

The two main products of MTBE splitting are the $C_4$ compound isobutylene and methanol. The further $C_4$ compound tertiary-butanol can also be comprised in the splitting reaction product phase. Either or both of isobutylene and tertiary-butanol can be supplied as feed to process step a1) to make up the total $C_4$ compound content of the feed for this process step or in addition to further $C_4$ content from another source. One or more intermediate separation and/or purification steps are also possible between the splitting of MTBE and the supplying of the thus-obtained at least one $C_4$ compound to the gas phase oxidation in process step a1), for example, to separate as far as possible the at least one $C_4$ compound and methanol from each other and to remove any side products from the splitting which might adversely affect the gas phase oxidation. Separation and/or purification can be by any means known to the skilled person and appearing suitable. Suitable purification and separation processes are described, for example, in EP 1 149 814 A1, WO 04/018393 A1 and WO 04/052809A1. After separation of methanol, the splitting phase which comprises the $C_4$ compound isobutylene as main component can then be optionally purified and provided as feed to process step a1). Suitable purification methods are known to the person skilled in the art and preferably comprise at least one of distillation, extraction, adsorption, absorption, chromatography or washing, preferably at least one of distillation and extraction, preferably at least one distillation and at least one extraction. Unreacted MTBE can be at least partially separated from the $C_4$ compound phase in this step. Separated MTBE can be optionally purified and at least partially recycled to the splitting reaction.

In a preferred embodiment of the process according to the invention, the methanol obtained in process step aa1) is supplied to process step g). In another aspect of the process according to the invention, the methanol obtained in process step aa1) can be supplied to process step a5). The methanol can optionally be purified, preferably by means of a thermal purification such as distillation, fractionation or rectification, crystallisation, extraction, column or washing, more preferably at least one distillation. An example of a purification of methanol is described in EP 1 254 887.

The invention also relates to a device for production of at least one of methacrylic acid and a methacrylic acid ester, comprising at least the following components in fluid-conducting communication with each other:

A1) a gas phase oxidation unit (A1), comprising a methacrolein providing unit, wherein the methacrolein is obtained by the heterogeneously catalysed gas phase oxidation of a $C_4$-source
F3) a methacrolein providing unit (F3), wherein the methacrolein is obtained by the reaction of propionaldehyde with a $C_1$ extending agent, which feeds in the gas phase oxidation unit (A1)
A2) a quench unit,
A3) a first extraction unit,
A4) a first separation unit,
A5) optionally, a first esterification unit,
B) a second separation unit,
C) optionally, a third separation unit,
D) optionally, a fourth separation unit,
wherein the first separation unit is a thermal separation unit with at least one bottom outlet in the lower third thereof, the at least one bottom outlet being in fluid-conducting communication with at least one inlet of the second separation unit.

The term "in fluid-conducting communication" is understood here as meaning that the units are connected such that a fluid, which can be at least one of a liquid, a gas, a vapour, a supercritical fluid or any other fluid, can be conducted from one unit to at least one other unit. This can be achieved, for example by direct communication via tubes or pipes, for example made of a material which is resistant to the reagents and conditions prevailing, such as stainless steel or glass, or any other suitable material known to the skilled person, or indirectly by means of tank vehicles or a tank or reservoir arranged between units. If a gas is to be conducted and should remain in gaseous form, the means of conducting the gas is preferably maintained at a temperature above the dew point of the gas. If a liquid is to be conducted, the means of conducting the liquid is preferably maintained at a temperature above the solidification and/or precipitation point of the liquid and/or components present in the liquid. This can be achieved by means of insulating and/or heating the means of conducting the respective gas or liquid. All reactors, columns, and other device components are preferably made from a material which is resistant to the reagents and conditions, such as temperature and pressure conditions in particular, to which they are subjected.

The gas phase oxidation unit A1) preferably comprises at least one reactor suitable for carrying out a gas phase reaction, in particular a pressure reactor, preferably at least one multitube reactor, formed for example as a tube and shell reactor, and/or at least one plate reactor and/or at least one fluidised bed reactor, whereby a multitube reactor is preferred. Particularly preferred is at least one multitube reactor in which oxidation catalyst is arranged in at least one tube, preferably wherein the tubes are packed or coated, preferably packed, with oxidation catalyst. Oxidation catalysts preferred according to the invention are those mentioned above in connection with the inventive process. The reactor materials should be resistant and preferably inert to the reagents and prevailing conditions inside the reactor. Suitable reactors are commercially available, for example from MAN DWE GmbH, Deggendorfer Werft, Germany, or from IHI Corporation, Japan, and form part of the general knowledge of the person skilled in the art.

In a two stage gas phase oxidation, the gas phase oxidation unit can comprise at least two reaction zones, each comprising oxidation catalyst. The at least two reaction zones can be at least two reaction zones in a single reactor, or at least two reactors. The oxidation catalyst in a first reaction zone is preferably an oxidation catalyst for oxidation of at least one $C_4$ compound, preferably isobutylene and/or tert-butanol, to methacrolein, and the oxidation catalyst in a second reaction zone is preferably suitable for oxidation of methacrolein to methacrylic acid. Suitable catalysts are mentioned above in connection with the process according to the invention.

The second methacrolein comprising feed stream obtained by the reaction of propionaldehyde with a $C_1$ extending agent, preferably formaldehyde, is fed into the two stage gas phase oxidation unit between the first reaction zone and the second reaction zone, that means after the oxidation catalyst of the first reaction zone and before the oxidation catalyst of the second reaction zone.

In a preferred aspect of the apparatus of the present invention, at least one supply for at least one source of oxidant, preferably oxygen, preferably air, and at least one supply for water and/or steam, are in fluid communication with the gas phase oxidation unit. If the gas phase oxidation unit comprises at least a first and a further oxidation area, the apparatus can comprise, for each oxidation area, at least one supply for at least one oxidant source and at least one supply for water and/or steam. The apparatus can further comprise a supply for a diluent such as nitrogen, argon and/or carbon dioxide, preferably nitrogen or carbon dioxide, for example carbon dioxide-comprising recycle gas from a catalytic combustion unit (CCU) or a thermal combustion unit (TCU), preferably a CCU or a TCU downstream in the device according to the invention. The respective supplies should be made of a material which is resistant to the reagents and conditions prevailing, for example, stainless steel or glass. In a preferred design the oxygen, diluent and water are supplied to the $C_4$ flow before entry into the respective reactor, so that a pre-formed mixture enters the reactor.

Step a1) of the process according to the invention is preferably carried out in the gas phase oxidation unit.

In a preferred embodiment of the apparatus according to the invention, the quench unit A2) is an absorption unit in which the gaseous oxidation phase is condensed and/or absorbed to form a liquid phase. It is preferred that methacrylic acid present in the oxidation phase leaving the catalytic reaction zone is condensed in the quench unit A2) to form a solution, preferably an aqueous solution, comprising methacrylic acid as main oxidation product. Unreacted methacrolein can also be separated in the absorption unit A2) and, if desired, conducted back to the gas phase oxidation zone for further reaction. Quench units suitable for use in the apparatus according to the invention are known to the skilled person. Step a2) of the process according to the invention is preferably carried out in the quench unit A2).

In a preferred embodiment of the device according to the invention, the quench unit A2) is followed by a first extraction unit A3). The methacrylic acid-comprising aqueous solution formed in the quench unit A2) is conducted to the first extraction unit A3), where an organic solvent is provided, into which solvent methacrylic acid is preferably substantially extracted. The organic solvent is preferably substantially immiscible with water, so that an aqueous phase which is at least partially depleted in methacrylic acid, and a methacrylic acid-comprising organic phase are formed. Details regarding preferred organic solvents are given above in the description of process step a3). Process step a3) is preferably carried out in the first extraction unit.

Any extraction unit known to the skilled person and appearing suitable for such an extraction of methacrylic acid can be considered for use as the first extraction unit A3).

The device according to the invention comprises first separation unit A4) downstream of the first extraction unit A3). If the device according to the invention is for production of methyl methacrylate, the first separation unit A4) is preferably upstream of the first esterification unit A5), preferably between and in fluid communication with the first extraction unit A3) and the first esterification unit A5). The first separation unit A4) is preferably suitable for separation and preferably purification of methacrylic acid, in particular for separation of methacrylic acid from the extraction agent used in the first extraction unit A3), and preferably also allows separation of methacrylic acid from other components present in the crude organic phase exiting the first extraction unit A3) of the device according to the invention, corresponding to the crude organic phase of process step a3) of the process according to the invention. The first separation unit A4) is preferably a thermal separation unit, preferably comprising at least one of a distillation column, a fractionating column, a rectification column, and any other thermal separation means known to the skilled person and appearing suitable for the separation of process step a3) of the inventive process. It is possible that the first separation unit A4) comprises more than one separation stage. The first separation unit A4) preferably comprises at least one bottom outlet, which can be an outlet at the bottom or in the lower third of the first separation unit. This arrangement of the first separation unit A4) preferably allows the separation of a high boiler phase from the crude organic phase, corresponding to process step aa4) of the process according to the invention. The at least one bottom outlet is preferably in fluid-conducting communication with at least one inlet of the second separation unit B). This fluid-conducting communication can be by means of a direct conduit between the at least one bottom outlet of the first separation unit and at least one inlet of the second separation unit. It is also possible that at least one intermediate device and/or component R) is arranged between the at least one bottom outlet of the first separation unit and the at least one inlet of the second separation unit B), for example at least one further separation device, such as at least one further thermal separation device and/or at least one solid/liquid separating device, and/or at least one mixing device and/or at least one reservoir, for example to enable an introduction of the high boiler phase separated in the first separation unit A4) to the first aqueous phase, preferably a combination of the high boiler phase with the first aqueous phase, and optionally a separation of components of the high boiler phase and/or of the combined high boiler phase and first aqueous phase. Any devices and components known to the skilled person and appearing suitable for the described purposes may be comprised in the device according to the invention.

An optional first purification unit for purification of methacrylic acid separated in the first separation unit A4) may also be arranged downstream of the first separation unit A4). The optional first purification unit can be, for example, a thermal purification unit, such as a distillation column, a fractionation column, a rectification column or the like, a crystallisation unit, or any other device known to the skilled person and appearing suitable for purification of methacrylic acid.

It is possible for the device according to the invention to further comprise one or more additional components between any or all of the units or components mentioned, for example thermal or stripping means for separating high and/or low boiling components, means for solid/liquid separation, such as at least one filter and/or centrifuge, and/or cooling and/or heating units. In a preferred design, for example, a distillation column for low boilers and optionally also a filter are arranged downstream of the quench unit and upstream of the extraction unit. In a further preferred aspect of a two-stage gas phase oxidation unit, a quench unit is arranged between the two stages.

Unreacted methacrolein can be separated in any of the quench unit, the first extraction unit, the first separation unit, the first purification unit, or any of the above-mentioned further device components, and conducted back to the gas phase oxidation unit for further reaction.

A first esterification unit A5) can be arranged downstream of the first separation unit A4) or the optional first purification unit. The first esterification unit A5) is not particularly limited and can be any unit suitable for esterification to form a methacrylate ester, preferably methyl methacrylate, from methacrylic acid. It is preferably suitable for liquid phase esterification. The first esterification unit A5) preferably comprises an esterification catalyst, which can be a heterogeneous or homogeneous catalyst such as a solid state catalyst or a liquid catalyst, and is preferably an acidic ion exchange resin such as those described in U.S. Pat. No. 6,469,292, JP 1249743, EP 1 254 887 or commercially available under the trade name names Amberlyst® (Rohm and Haas Corp.), Dowex®, (Dow Corp.) or Lewertit® (Lanxess AG), or an acid capable of catalysing esterification, such as sulphuric acid, $H_2SO_4$.

A second purification unit can be arranged downstream of the first esterification unit A5), for purification of the methacrylate ester produced therein. The optional second purification unit can be, for example, a thermal purification unit, such as a distillation column, a fractionation column, a rectification column or the like, a crystallisation unit, or any other device known to the skilled person and appearing suitable for purification of methacrylic ester, in particular methyl methacrylate.

The device according to the invention further comprises a second separation unit B). The second separation unit B) serves to separate at least a part of the water comprised in the first aqueous phase obtained in the first extraction unit A3) from at least a part of at least one organic compound, in particular at least one component ii. as described above, to obtain a second aqueous phase and an organic phase. Process step b) of the process according to the invention is preferably carried out in second separation unit B).

In a preferred embodiment of the device according to the invention, the second separation unit B) comprises a second extraction unit B1). The second extraction unit B1) serves to extract a least a part of the first aqueous phase with an extraction agent to form a second aqueous phase and an extraction phase, as well as preferably serving to separate the second aqueous phase from the extraction phase to the greatest extent possible within the technical limitations. Thus at least process step b1a) and preferably process steps b1a) and b1b) of the process according to the invention are preferably carried out in the second extraction unit B1), most preferably in a continuous fashion. The second extraction unit B1) preferably comprises at least one extraction column, washing column, phase separator or other device known to the skilled person and appearing suitable for liquid-liquid extraction, and preferably also suitable for separation of an organic phase or an ionic liquid phase from an aqueous phase, more preferably for extraction and separation in a continuous process, for example at least one extraction column, at least one pulsed fill and/or packing column, at least one rotating extractor, in particular at least one rotating extractor using centrifugal force for separation, at least one washing column, and/or at least one phase separator. The second extraction unit B1) is preferably capable of withstanding and of operating at ambient temperatures, as well as at temperatures other than ambient temperatures, in particular at elevated temperatures, in particular at the temperatures mentioned above in connection with the process steps b1a) and b1b).

In another preferred embodiment of the device according to the invention, the second separation unit comprises
B2a) a crystallisation unit, and
B2b) optionally, a crystal separation unit.

In the crystallisation unit B2a), the first aqueous solution obtained in the first extraction unit is generally cooled so that water at least partially crystallises out. The resulting slurry may then be conveyed, optionally via a residence unit T1) for crystal growth, as described above in connection with process steps b2a) and b2b), to a crystal separation unit B2b), for example a wash column or a centrifuge, where the solid crystals are at least partially separated from the mother liquor, and preferably washed to at least partially remove remaining impurities to the greatest extent possible. At least one melting device may also be comprised in the second separation unit B2), and may be internal or external to at least one of the crystallisation unit B2a) and the crystal separation unit B2b), preferably being in fluid- and/or solid-conducting communication with at least the crystal separation unit B2b). At least a part of the optionally washed crystals is preferably melted in the at least one melting unit and at least a part of the melted part either passed to the next device component or used as wash liquid for the crystals in the crystal separation unit, or both. It is also possible that at least a part of the crystals is supplied, by means of one or more conduits, from the crystal separation unit B2b) to the crystallisation unit B2a) and/or to the residence unit T1) as crystallisation seed.

Any crystallisation units, residence units and crystal separation units known to the skilled person and appearing suitable for the above-described purposes can be used in the device according to the invention, whereby respective units allowing a continuous crystallisation and separation are preferred. The crystallisation unit can be any crystallisation unit known to the skilled person and appearing suitable for crystallisation of water from an aqueous solution comprising organic components, whereby suspension crystallisation units are preferred, and even more preferred are suspension crystallisation units equipped with a scraper for at least partially scraping crystals off of cooled surfaces on which they may form. The residence unit, if provided, is preferably in the form of a tank, preferably equipped with stirring means, and with at least one inlet in fluid- and/or solid-conducting communication with the crystallisation unit and at least one outlet in fluid- and/or solid-conducting communication with the crystal separation unit. The crystallisation unit, optionally together with the residence unit, is preferably suitable for carrying out step b2a) of the process according to the invention. The crystal separation unit is preferably suitable for carrying out step b2b) of the process according to the invention, and is preferably a wash column or a centrifugation device. Suitable crystallisation units, as well as crystallisation units incorporating wash and/or melt units are, for example, suspension crystallisation units with downstream washing of the crystals in an hydraulic or mechanical wash column as described in the book "Melt Crystallisation Technology" by G. F. Arkenbout, Technomic Publishing Co. Inc., Lancaster-Basel (1995), pp. 265-288, in Chem. Ing. Techn. (72) (10/2000), 1231-1233. Generally, any wash melt wash columns with forced transport, eg described in Chem. Ing. Techn. 57 (1985) No. 2, p. 91-102 and Chem. Ing. Techn. 63 (1991), No. 9, p. 881-891 and in WO 99/6348. Examples of suitable wash melt columns are described in EP 97405, U.S. Pat. No. 4,735,781, WO 00/24491, EP 920894, EP 398437, EP 373720, EP 193226, EP 191194, WO 98/27240, EP 305316, U.S. Pat. No. 4,787, 985, and are commercially available, for example from the TNO Institute in Apeldoorn, Netherlands, from Niro Process Technology B.V., Hertogenbosch, NL, or from Sulzer Chemtech AG, Switzerland, TNO or Niro Process Technology B.V., The Netherlands. Further examples of suitable crystallisation units, wash units and melting units, as well as combined crystallisation/wash/melt units are also given in the literature cited above in connection with process step b2a). Centrifugation devices suitable as crystal separation units in the device according to the invention are known to the skilled person.

At least one incinerator or combustion unit may be comprised in the device according to the invention, for example for incineration of the extraction phase obtained in the second extraction unit or of the mother liquor obtained from the crystallisation unit and/or the crystal separation unit.

The device according to the invention can further comprise a third separation unit C). Third separation unit C) is preferably comprised in particular in the embodiment wherein the device according to the invention comprises an extraction unit as second separation unit, but may also be comprised in the embodiment wherein the device according to the invention comprises a crystallisation unit as second separation unit. Third separation unit C) preferably serves to separate any remaining extraction agent used in process step b1a) from the second aqueous phase. Third separation unit C) may be a further extraction unit, but is preferably a thermal separation unit, for example a distillation column, a fractionating column, a rectification column or the like, whereby any means known to the skilled person and appearing suitable for such a separation may be considered in the device according to the invention.

The device according to the invention can also further comprise a fourth separation unit D). In the embodiment in which the second separation unit B) comprises an extraction unit B1a), the fourth separation unit D) preferably comprises at least one thermal separation device D1a) for separation of at least a part of the extraction agent from the extraction phase to obtain an extract comprising at least one component ii. according to the invention, corresponding to process step d1a). At least one further thermal separation device D1b) may also be comprised for separation of at least a part of a least one component ii. according to the invention from the extract, corresponding to process step d1b). Thermal separation devices known to the skilled person and appearing suitable for carrying out the separations of process steps d1a) and d1b) can be considered for use in the device according to the invention, such as at least one of distillation, fractionation or rectification columns, or the like.

In the embodiment in which the second separation unit comprises a crystallisation unit and a crystal separation unit, the fourth separation unit D) preferably comprises at least one of a dewatering unit D2a) and a further separation unit D2b). The dewatering unit D2a) is preferably suitable for carrying out process step d2a) of the inventive process. Dewatering units which are known to the skilled person and appear suitable for at least partial dewatering of the mother liquor separated in the crystallisation unit and/or the crystal separation unit can be considered for use in the device according to the invention. Preferred dewatering units according to the invention are, for example, columns packed with a dehydration agent which does not react with at least one component ii., such as molecular sieves, and distillation units, in particular distillation units which are suitable for azeotropic distillation. The further separation unit D2b) is preferably suitable for carrying out step d2b) of the process according to the invention, and is preferably a thermal separation unit. Thermal separation devices known to the skilled person and appearing suitable for carrying out the separations of process steps d1a) and d1b) can be considered for use in the device according to the invention, such as at least one of distillation, fractionation or rectification columns, or the like.

Further separation units may also be comprised in the device according to the invention. One example of a preferred further separation unit is a separation unit suitable for separating at least one component ii. from a mixture comprising at least two components ii. according to the invention, for example a mixture obtained in step d) of the process according to the invention. Such further separation units are preferably thermal separation units, preferably comprising at least one distillation column, fractionation column, rectification column, or the like.

The device according to the invention preferably comprises at least one conduit between at least one of the fourth separation unit D) and at least one further separation unit, and first extraction unit A3) and/or first separation unit A4), for conducting at least one of methacrylic acid and a methacrylic acid-comprising phase from at least one of the fourth separation unit D) and at least one further separation unit back to at least one of the first extraction unit A3) and the first separation unit A4).

The device according to the invention optionally comprises at least one second esterification unit G) for esterification of at least one component ii., preferably downstream of at least one of the second separation unit B), the third separation unit C) and the fourth separation unit D). Process step g) of the inventive process is preferably carried out in second esterification unit G). The details concerning the second esterification unit G) are the same as those mentioned above for the first esterification unit A5).

The device according to the invention can also comprise at least one ester separation unit H) for at least partial separation of one or more esters from each other, in particular for at least partial separation of at least one ester from the ester phase obtained in the at least one second esterification unit G), corresponding to process step h) of the inventive process. Any device known to the skilled person and appearing suitable for separation of esters may be used as ester separation unit H). Thermal separation devices of the types already mentioned, as well as crystallisation devices, extraction devices, phase separation devices are preferred as ester separation unit in the device according to the invention.

At least one further purification unit J) may also be provided in the device according to the invention, for purification of the ester and/or esters obtained in the second esterification unit G) or separated in the at least one ester separation unit H). Process step j) of the process according to the invention is preferably carried out in the at least one further purification unit J). The details of this further purification unit correspond to those for the purification unit mentioned in connection with the first esterification unit.

The device according to the invention may also comprise at least one ester conduit between the second extraction unit B1), if comprised, and at least one of the second esterification unit G), the ester separation unit H) and the further purification unit J) for purification of at least one ester. The at least one ester conduit serves to conduct at least one ester from at least one of the second esterification unit G), the ester separation unit H) and the further purification unit J) for purification of at least one ester to the second extraction unit B1a), where the at least one ester can optionally be used as extraction agent.

In a preferred aspect of the device according to the invention, the device further comprises an MTBE splitting unit AA1) upstream of the gas phase oxidation unit A1). Splitting units and suitable catalysts for MTBE splitting are well known in the art and form part of the general knowledge of the skilled person, as described, for example, in Ullmann's Encyclopedia of Industrial Chemistry, $5^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, $5^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein.

An isobutylene separation unit S1) is preferably arranged between the MTBE splitting unit AA1) and the gas phase oxidation unit A1) and in fluid-conducting communication with each. The isobutylene separation unit S1) serves to separate an isobutylene phase and preferably also a methanol phase from the effluent of the second catalytic reaction zone, which effluent comprises isobutylene and methanol as principal components. The isobutylene separation unit S1) can be at least one of an extractor, a crystalliser, a column, a distillation device, a rectification device, a membrane, a pervaporation device, a phase separator and a wash device. The isobutylene separation unit S1) preferably comprises an outlet for an isobutylene phase and an outlet for a methanol phase. The outlet for an isobutylene phase is preferably connected to the gas phase oxidation unit A1), optionally via an intermediate unit such as a purification unit, a heat exchanger, and/or a pressuriser. The outlet for a methanol phase is preferably connected to at least one of the first esterification unit and the second esterification unit, optionally via an intermediate methanol purification unit. Any device known to the skilled person and appearing suitable for purification of methanol may be comprised as methanol purification unit. Examples of suitable purification units preferably comprise at least one distillation device, crystalliser, extractor, column or wash device, more preferably at least one distillation device. An example of a purification unit for methanol is described in EP 1 254 887.

The invention also relates to a process according to the invention, wherein the process takes place in a device according to the invention.

The invention is more closely illustrated by the following figure and non-limiting examples.

Figure 1:
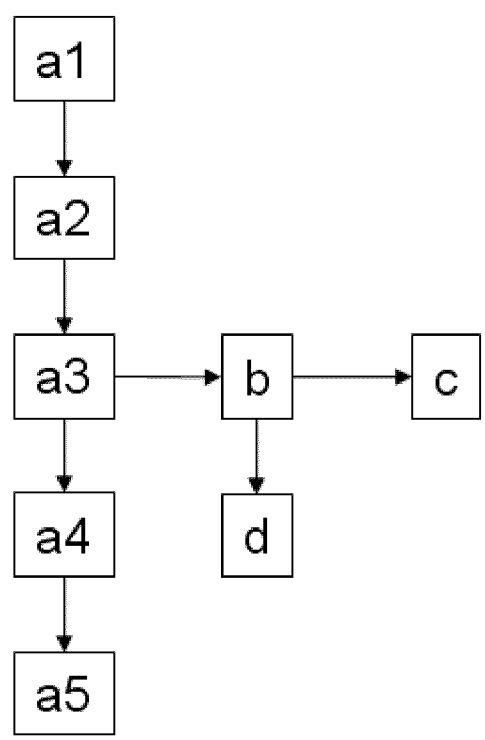
FIG. 1 shows schematically a preferred embodiment of the process according to the invention in the form of a flow diagram.
Figure 2:
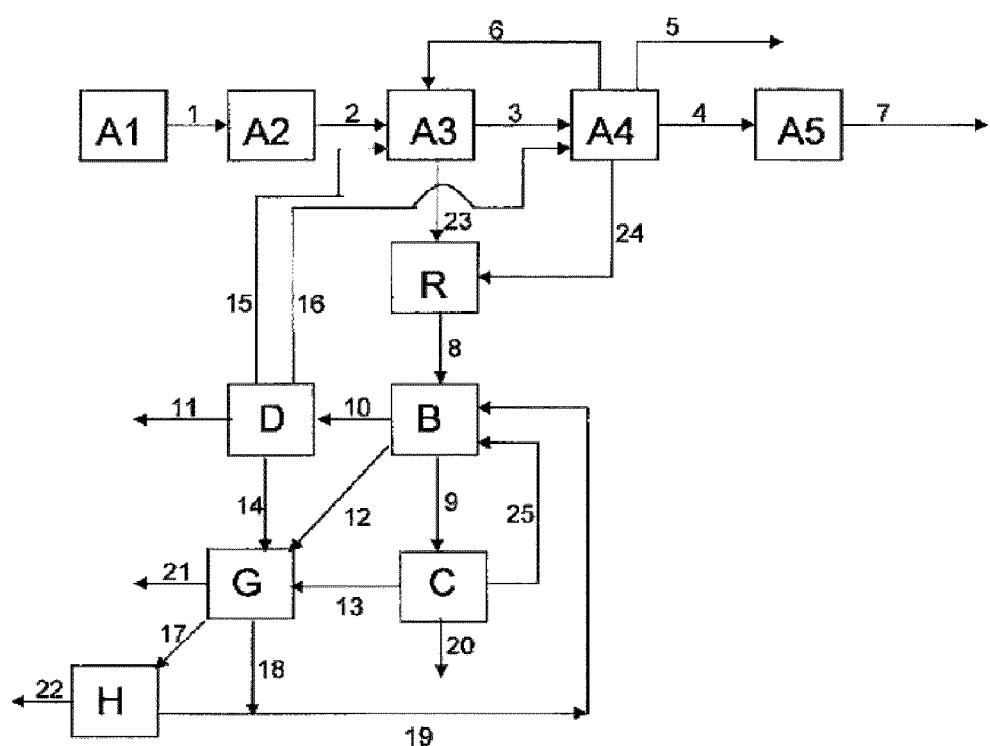
FIG. 2 shows schematically an embodiment of the device according to the invention in which second separation unit B is an extraction unit.

According to the embodiment of FIG. 2, a $C_4$ compound is introduced into gas phase oxidation unit A1 where it is oxidised in a one- or two-stage catalytic gas phase oxidation to methacrylic acid. Inlets into gas phase oxidation unit A1 for $C_4$ compound, oxygen, steam and inert diluent gas are not shown. The $C_4$ compound can be provided from an MTBE splitting unit AA1 (not shown), via an isobutylene separating unit S1 (not shown). The gaseous methacrylic acid phase obtained in gas phase oxidation unit A1 is conducted via line 1 to quench unit A2, where it is cooled and absorbed into water or an aqueous phase to form an aqueous methacrylic acid-comprising phase. An inlet for the quench liquid into quench unit A2 is not shown. The aqueous methacrylic acid phase is conducted via line 2 to first extraction unit A3, where it is extracted with an organic solvent as extraction agent to form an organic phase and an aqueous phase (the first aqueous phase of the process according to the invention). These two phases are separated in first extraction unit A3.

The organic phase from first extraction unit A3 is conducted via line 3 to first separation unit A4, where it is distilled to separate methacrylic acid and extraction agent, as well as a high boiler phase. The extraction agent can be recycled via line 6 to first extraction unit A3. The methacrylic acid can be collected via line 5 and optionally purified in downstream purification unit or units (not shown), or it can be conducted via line 4 to first esterification unit A5, optionally via a purification (not shown). In first esterification unit A5, the methacrylic acid can be esterified, for example with methanol, for example methanol separated from an MTBE splitting phase in separating unit S1 (not shown), to form methyl methacrylate. It is also possible to esterify methacrylic acid in first esterification unit A5 with other alcohols as mentioned above. The ester produced in first esterification unit A5 is collected via line 7 and can be optionally polymerised in polymerisation unit A6 (not shown), optionally with intermediate and/or downstream purification. The high boiler phase collected in first separation unit A4 is conducted to second separation unit B, optionally via combination unit R where it can be combined with the aqueous phase separated in first extraction unit A3 if so desired.

The aqueous phase separated in first extraction unit A3 is conducted to second separation unit B (direct conduit not shown), optionally via line 24 and combination unit R, where it can be combined with the high boiler phase if so desired. Combination unit R may also be omitted, and the aqueous phase and the high boiler phase combined directly with each other in second separation unit B.

The combined aqueous phase and high boiler phase is extracted in second separation unit B with an organic solvent as second extraction agent to form an aqueous phase (corresponding to the second aqueous phase of the inventive process) and an organic phase. The aqueous phase is conducted via line 9 to third separation unit C, where remaining extraction agent from the second extraction step can be at least partially separated and optionally recycled via line 25 to second separation unit B. The remaining aqueous phase, corresponding to the third aqueous phase of the inventive process, can be recycled, for example to gas phase oxidation unit A1 (conduit not shown), used as process water, conducted to a biological purification unit (not shown) or discharged, via line 20. The organic phase separated in second separation unit B can be conducted via line 10 to fourth separation unit D, where at least one component ii. can be separated. At least a part of the at least one component ii. separated in fourth separation unit D can be collected via line 11 and optionally purified (not shown). If a mixture of components ii. is separated in fourth separation unit D, this mixture can be conducted to a further separation unit for separation of components ii. from each other (not shown). If methacrylic acid or a methacrylic acid-comprising phase is separated in fourth separation unit D, this methacrylic acid or methacrylic acid-comprising phase can be conducted via line 15 to first extraction unit A3 or via line 16 to first separation unit A4. It is also possible that at least a part of the at least one component ii. separated in fourth separation unit D is conducted via line 14 to second esterification unit G. Either of the organic and aqueous phases separated in second separation unit B, or the aqueous phase separated in third separation unit C, may be conducted to second esterification unit G. In second esterification unit G at least one component ii. is esterified with an alcohol to form a corresponding ester. If the alcohol is methanol, this methanol can, for example, be introduced from MTBE splitter AA1 via separation unit S1, optionally with intermediate purification (not shown). If the ester phase obtained in second esterification unit G comprises more than one ester, at least one ester can be separated in ester separation unit H. At least one ester can be purified in downstream ester purification unit J (not shown). At least one ester obtained in one or more of the second esterification unit G, the ester separation unit H and the ester purification unit J can be conducted to second separation unit B for use as extraction agent.

Figure 3:
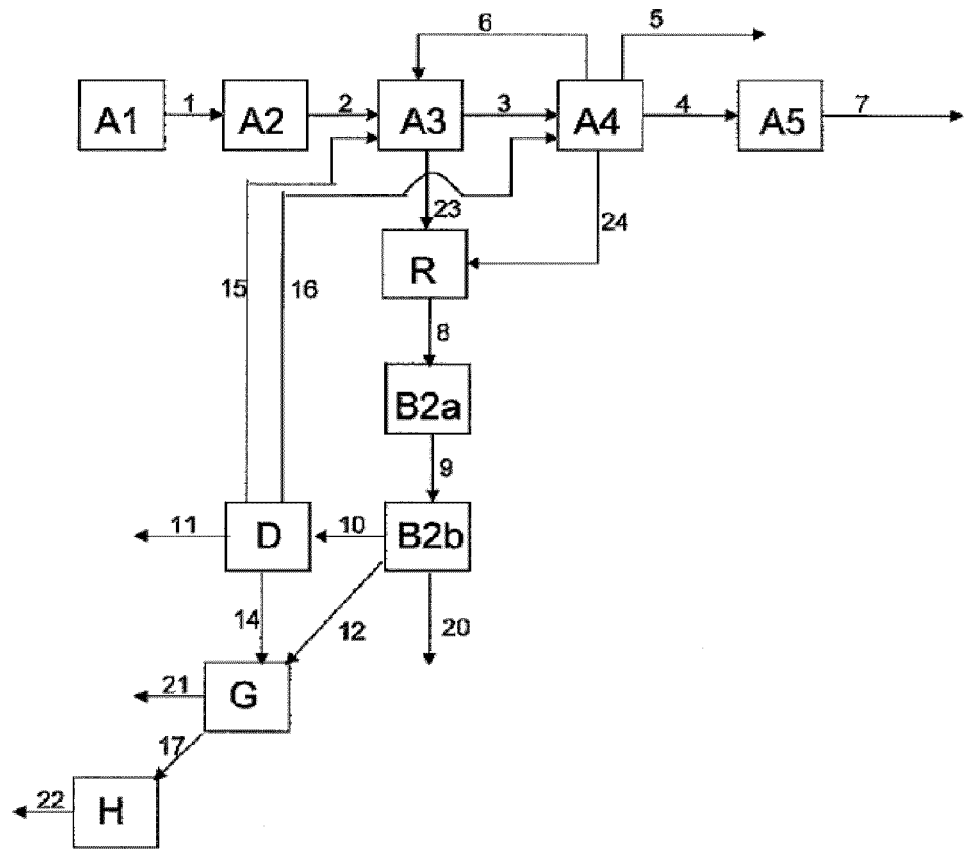
FIG. 3 shows schematically an embodiment of the device according to the invention in which second separation unit B is a crystallisation unit.

FIG. 3 shows another embodiment of the device according to the invention in which second separation unit B is a crystallisation unit. In this embodiment, the details concerning device components A1 to A6, R, G, H, J, AA1 and S1 are the same as in the embodiment of FIG. 2 and only the different aspects are described in the following. In the embodiment exemplified in FIG. 2, the combined aqueous phase and high boiler phase is generally cooled in the crystallisation unit B2a so that water at least partially crystallises out. If crystals form at least partially on cooled surfaces of the crystallisation unit B2a, these can be scraped off. The resulting slurry is then optionally conducted to a residence unit T1 (not shown), where the slurry is preferably stirred while more crystals grow and/or crystal size increases. From the crystallisation unit B2a and/or the residence unit T1 the slurry of crystals and mother liquor is then conducted via line 9 to the crystal separation unit B2b, where the solid crystals are at least partially separated from the mother liquor and optionally washed to at least partially remove impurities. A part of the crystals may be conducted back from crystal separation unit B2b to crystallisation unit B2a and/or to residence unit T1 to act as crystal seed (conduit not shown).

At least a part of the optionally washed crystals can be melted and at least a part of the melted part can be recycled, for example to gas phase oxidation unit A1 (conduit not shown), used as process water, used as wash liquid for washing the crystals in the crystal separation unit B2a, conducted to a biological purification unit (not shown) or discharged, via line 20, The mother liquor separated in crystal separation unit B2b can be conducted via line 10 to fourth separation unit D, where at least one component ii. can be separated. Fourth separation unit D can comprise a dewatering unit D2a and/or a thermal separation unit D2b.

If a mixture of components ii. is separated in fourth separation unit D, this mixture can be conducted to a further separation unit for separation of components ii. from each other (not shown). If methacrylic acid or a methacrylic acid-comprising phase is separated in fourth separation unit D, this methacrylic acid or methacrylic acid-comprising phase can be conducted via line 15 to first extraction unit A3 or via line 16 to first separation unit A4. At least a part of the at least one component ii. separated in fourth separation unit D can be collected via line 11 and optionally purified in a further purification unit (not shown). It is also possible that at least a part of the at least one component ii. separated in fourth separation unit D is conducted via line 14 to second esterification unit G. The mother liquor separated in crystal separation unit B2b may be conducted to second esterification unit G.

Figure 5:
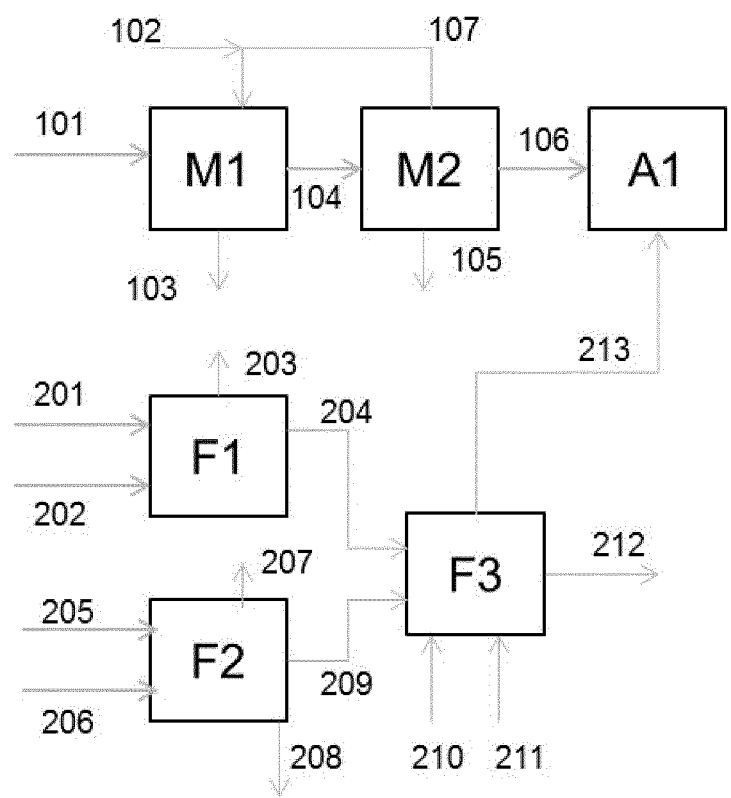
FIG. 5 shows schematically the process according to the invention, having both a $C_4$ and a $C_2$ based methacrolein synthesis branch, in the form of a flow diagram.

FIG. 5 shows the process according to the invention, having both a $C_4$ and a $C_2$ based methacrolein synthesis branch. Crude C4 containing Isobutene is fed via Line 101 to MTBE synthesis (M1). Methanol (fresh) and recycled Methanol line 102 and 107 are also fed to M1. Treated C4 goes via line 103 to a Cracker or an olefin treating unit (not shown). MTBE as product goes via line 106 from M1 to the MTBE splitter M2. Highboilers (line 105) and methanol (line 107) are withdrawn from M2. Pure Isobutene is fed to Oxidation A1 via line 106.

Methanol (via line 201) and air (via line 202) are fed to Formalin synthesis (F1). Tail gas is withdrawn from F1 via line 203 and has to be treated (not shown). Formalin is fed via line 204 to Methacrolein-synthesis (F3). Ethylene is fed via line 205 to Propionaldehyde-Synthesis (F2). Synthesis gas (a mixture from Hydrogen and Carbon monoxide) is fed via line 206 to Propionaldehyde synthesis. Tail gas is withdrawn via line 207 and has to be treated (not shown). High boilers are withdrawn from F2 via line 208. Propionaldehyde is fed to the Methacrolein synthesis (F3) via line 209. Carbonic acid (210) and secondary amine (e.g. Dimethyl amine) (211) are fed to F3. A waste water (212) is withdrawn from F3 and has to be treated. Methacrolein (213) is fed to Oxidation A1.

M1: MTBE Synthesis
M2: MTBE Splitter
F1: Formalin Synthesis
F2: Propionaldehyde Synthesis
F3: Methacrolein Synthesis
Streams
101: Crude C4 with Isobutene
102: Methanol (Makeup)
103: Treated C4
104: MTBE
105: Highboilers
106: Isobuten
107: Methanol
201: Methanol to Formalin synthesis
202: Air to Formalin synthesis
203: Exhaust Air
204: Formalin
205: Ethylene
206: Carbon monoxide/Hydrogen
207: Exhaust-Air
208: Highboilers
209: Propionaldehyde
210: Carbonic Acid
211: Dimethyl amine
212: Waste water
213: Methacrolein to Oxidation
Test Methods
Measurement of Partition Coefficient (k Value)

An aqueous phase comprising a pre-determined amount of acetic acid is combined with the same volume of an organic solvent (extraction agent). The two phases are shaken and/or stirred for 15-30 minutes at 50° C. to ensure that the equilibrium distribution of acetic acid over the aqueous and organic phases is achieved. The mixture is then allowed to separate back into organic and aqueous phases at 50° C. and these two phases are separated from each other. The amount of acetic acid present in the separated organic phase is measured by gas chromatography (GC) or high pressure liquid chromatography (HPLC).

| | | | |
|---|---|---|---|
| HPLC: | | Agilent 1200 | |
| Pump: | | Quaternary Pump | |
| Eluent: | | Acetonitrile $KH_2PO_4$ (0.02 mol/L) pH 2 | |
| | Gradient | 3 min | 0% 100% |
| | | 15 min 50% | 50% |
| | | 30 min 70% | 30% |
| Flow: | | 1.0 ml/min | |
| Stop-Time: | | 30 min | |
| Post-Time: | | 5 min | |
| Control pressure: | | 190 bar, max. 250 bar | |
| Autosampler: | | Autosampler | |
| Injection volume: | | 20 µL | |
| Column oven: | | including column switch control | |
| Temperature: 30° C. | | | |
| Columns: | | Agilent SB-Aq | |
| | Maße | Length 150 mm, $d_i$ 4.6 mm, 3.5 µm Material | |
| Detector | | MWD or DAD | |
| UV | | 210 nm, 241 nm, 254 nm, 265 nm (DAD preferred) | |
| GC: | | Perkin Elmer Autosystem | |
| Autosampler: | | Perkin Elmer | |
| Cleaning solvent | | THF | |
| Injection volume | | 1.0 µL | |
| Injektor: | | | |
| Split | | split ratio 100 | |
| Temperature program | | 200° C. | |
| Flow | | constant Pressure 12.0 | |
| Column oven: | | | |
| Column | | J&W Scientific DB 225 | |
| Dimensions | | Lenght 30 m, $d_i$ 0.25 mm, 0.25 µm Material | |

-continued

| Temperature program | Rate | Temp. (° C.) | Stop-Time (min) |
|---|---|---|---|
| | Initial | 40 | 5.0 |
| | 15 | 180 | 4.0 |
| Running time: | 18.3 min | | |
| Detector | | FID | |
| Setpoint | | 260° C. | |

Example 1

Figure 4:
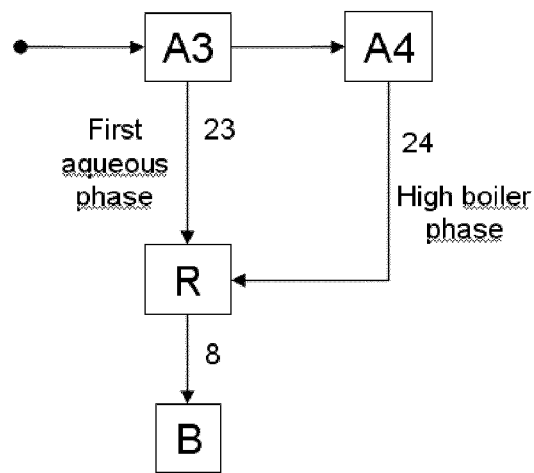
FIG. 4 shows schematically the combination of the first aqueous phase 23 from unit A3 with the high boiler phase 24 from unit A4 in the combination unit R.

Example 1 describes part of the process as shown in FIG. 4. The high boiler phase as generated on first separation unit A 4 containing 82.1 wt % MAA, 14.3 wt % various and partly unknown high boilers (dimeric and oligomeric MAA, maleic acid, terephthalic acid, citraconic acid, polymers etc.), and 3.6 wt % inhibitors (mainly Hydrochinon) is combined with the first aqueous phase as isolated from first extraction unit A3 containing 0.6 wt % MAA and 5.0 wt % high boilers in a ratio of high boiler phase to first aqueous phase of 1:80 in combination unit R. The concentrations in the resulting combined phase are measured to 1.6 wt % MAA and 5.1 wt % high boilers. The combined phase is extracted with n-hexane in a second separating unit B. Yielding 4.9 wt % MAA in the organic phase vs. 3.9 wt % MAA in the comparative case when the first aqueous phase is not combined with the high boiler phase.

Example 2

In a heatable two-step reactor (diameter: 16 mm) for the oxidation comprising an evaporator, a salt bath and a column of quenching following streams have been fed. A polyphosphoric molybdenum acid (composition: Mo(10)V(1)P(1)Cu(0.2)As(0.2)Ce(0.2)) was used as catalyst. The load of the catalyst in the second stage (oxidation to methacrylic acid) was 1580 $h^{-1}$.

Stream 1: Methacrolein (MAL) synthesized via an Aldol reaction with propionaldehyde and formaldehyde as educts, containing 0.7% by weight DIMAL (dimeric methacrolein), 1.5% by weight water and 0.1% propionaldehyde. This stream was evaporated and in a consecutive step to this stream oxygen, nitrogen and water in a ratio of 2.6 and 14 and 7 (referred to 1 part of MAL) were added.

Stream 2: MAL synthesized via a gas phase oxidation of tert-butanol has been fed as gas together with oxygen, nitrogen and water to the reactor. The ratio of MAL to air to nitrogen to water was 1 and 2.6 and 14 and 7.

For the examples corresponding to this invention the streams 1 and 2 have been brought together.

Comparative Example 2a) 100% Stream 1

Content of DIMAL: about 7000 ppm,
Temperature of the salt bath (for a conversion of 75%): 312.9° C.
Selectivity to methacrylic acid: 82.0%
Content of terephthalic acid (TPA) in the quenched liquid: 120 ppm
Minor clogging in the column; no downtime for cleaning was necessary.

Comparative Example 2b) 100% Stream 2

Content of DIMAL: about 110 ppm,
Temperature of the salt bath (for a conversion of 75%): 308.8° C.
Selectivity to methacrylic acid: 86.0%
Content of TPA in the quenched liquid: 1000 ppm,
Massive clogging (TPA) in the column; a downtime for cleaning was necessary after 10 days.

Example 2c) Mixture of Streams 1 and 2 in a Ratio (Referred to MAL) of 1 to 1

Content of DIMAL: 3300 ppm
Temperature of the salt bath (for a conversion of 75%): 311.5° C.
Selectivity to methacrylic acid: 83.8%
Content of TPA in the quenched liquid: about 400 ppm
Minor clogging in the column; a downtime for cleaning was necessary after 25 days.

Example 2d) Mixture of Streams 1 and 2 in a Ratio (Referred to MAL) of 21 to 79

Content of DIMAL: 300 ppm
Temperature of the salt bath (for a conversion of 75%): 309.7° C.
Selectivity to methacrylic acid: 85.5%
Content of TPA in the quenched liquid: about 600 ppm
Minor clogging in the column; a downtime for cleaning was necessary after 15 days.

Example 2e) Mixture of Streams 1 and 2 in a Ratio (Referred to MAL) of 78 to 22

Content of DIMAL: 6000 ppm
Temperature of the salt bath (for a conversion of 75%): 312.5° C.
Selectivity to methacrylic acid: 82.7%
Content of TPA in the quenched liquid: about 200 ppm
Minor clogging in the column; a downtime for cleaning was necessary after 50 days.

It is obvious for a person skilled in the art that a higher temperature of the salt-bath results in a shorter life-time of the catalyst. Therefore it was a surprising result of this invention that a combination of streams 1 and 2 affects a longer life-time of the catalyst in combination with less downtime.

The invention claimed is:
1. A process for preparing at least one of methacrylic acid and a methacrylic acid ester, the process comprising:
   a1) oxidizing a $C_4$ compound in a gas phase to obtain a reaction phase comprising methacrylic acid;
   a2) quenching the reaction phase to obtain a crude aqueous phase comprising methacrylic acid;
   a3) separating at least a part of the methacrylic acid from the aqueous phase comprising methacrylic acid to obtain at least one crude methacrylic acid-comprising phase;
   a4) separating and optionally purifying at least a part of the methacrylic acid from the crude methacrylic acid-comprising phase obtained in a3) via a thermal separation process;

a5) optionally esterifying at least a part of the methacrylic acid obtained in a4);

wherein the $C_4$ compound oxidised in a1) originates from a mixture of at least two different methacrolein comprising feed streams, and the mixture comprises 1 to 99 percent by weight of a first methacrolein comprising feed stream obtained by a heterogeneously catalysed gas phase oxidation of isobutylene or tert-butyl alcohol or isobutylaldehyde or a mixture of two or more thereof, and 99 to 1 percent by weight of a second methacrolein comprising feed stream obtained by reacting propionaldehyde with a $C_1$ extending agent.

2. The process according to claim 1, wherein the mixture comprises 5 to 95 percent by weight of the first methacrolein and 95 to 5 percent by weight of the second methacrolein.

3. The process according to claim 1, wherein the mixture comprises 20 to 80 percent by weight of the first methacrolein and 80 to 20 percent by weight of the second methacrolein.

4. The process according to claim 1, wherein a3) comprises extracting at least a part of the methacrylic acid from the crude aqueous phase comprising methacrylic acid into an organic solvent to obtain a crude organic phase comprising methacrylic acid and a first aqueous phase, wherein the first aqueous phase comprises components (i) at least 65 wt. % of water, based on a total weight of the first aqueous phase, and (ii) not more than 35 wt. % of at least one organic compound, based on the total weight of the first aqueous phase, wherein a total weight of (i) and (ii) is 100 wt. %.

5. The process according to claim 1, wherein the $C_4$ compound of the first methacrolein comprising feed stream is obtained by the heterogeneously catalysed gas phase oxidation of isobutylene, derived from splitting of methyl tert-butyl ether (MTBE) or ethyl tert-butyl ether (ETBE).

6. The process according to claim 1, wherein the methacrolein of the second methacrolein comprising feed stream is obtained by reacting propionaldehyde with formaldehyde.

7. The process according to claim 6, wherein the methacrolein of the second methacrolein comprising feed stream is obtained by reacting propionaldehyde with formaldehyde in the presence of a secondary amine and/or an acid.

8. The process according to claim 6, wherein the formaldehyde is obtained by oxidizing methanol in the presence of a molybdenum oxide or silver or silver oxide catalyst.

9. The process according to claim 1, wherein the propionaldehyde is obtained from ethylene and a synthesis gas in the presence of a rhodium and phosphorus comprising catalyst.

10. The process according to claim 1, wherein a quench liquid in a2) is water or at least a portion of a condensate formed in a2).

11. The process according to claim 1, wherein in a4) the methacrylic acid is purified via rectification to obtain a pure methacrylic acid, and the pure methacrylic acid is removed in a side outlet from a column used for the rectification.

12. The process according to claim 11, wherein the rectification in a4) is carried out at a bottom pressure in a range from 1 to 100 mbar.

13. The process according to claim 11, wherein the rectification in a4) is carried out at a bottom temperature in a range from 40 to 200° C.

14. The process according to claim 3, further comprising:

b) separating at least a part of the water comprised in the first aqueous phase obtained in a3) from at least a part of at least one component (ii) to obtain a second aqueous phase and an organic phase, wherein the organic phase comprises the at least one component (ii), and wherein the second aqueous phase is depleted in the at least one component (ii) compared to the first aqueous phase;

c) optionally separating at least a part of at least one organic compound from the second aqueous phase obtained in b) to obtain a third aqueous phase; and d) optionally separating at least a part of the at least one component (ii) from the organic phase obtained in b).

15. The process according to claim 1, comprising a5) esterifying at least a part of the methacrylic acid obtained in a4), to obtain a methacrylic acid ester.

16. The process according to claim 1, wherein the mixture comprises 22 to 79 percent by weight of the first methacrolein and 78 to 21 percent by weight of the second methacrolein.

17. The process according to claim 1, wherein the mixture comprises 50 to 79 percent by weight of the first methacrolein and 50 to 21 percent by weight of the second methacrolein.

* * * * *